(12) United States Patent
Kikuchi et al.

(10) Patent No.: US 9,510,736 B2
(45) Date of Patent: Dec. 6, 2016

(54) STEREOSCOPIC ENDOSCOPE DEVICE HAVING MECHANISM THAT CHANGES AN ANGLE BETWEEN OPTICAL AXES OF TWO IMAGING SENSORS

(71) Applicant: OLYMPUS CORPORATION, Tokyo (JP)

(72) Inventors: Satoru Kikuchi, Tokyo (JP); Hiroyoshi Kobayashi, Tokyo (JP); Hiromu Ikeda, Tokyo (JP); Osamu Konno, Saitama (JP); Shinya Fukushima, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 302 days.

(21) Appl. No.: 14/247,787

(22) Filed: Apr. 8, 2014

(65) Prior Publication Data

US 2014/0221748 A1    Aug. 7, 2014

Related U.S. Application Data

(63) Continuation of application No. PCT/JP2012/076871, filed on Oct. 11, 2012.

(30) Foreign Application Priority Data

Oct. 14, 2011    (JP) .................. 2011-227099

(51) Int. Cl.
*A61B 1/05*    (2006.01)
*A61B 1/06*    (2006.01)
(Continued)

(52) U.S. Cl.
CPC ....... *A61B 1/00193* (2013.01); *A61B 1/00006* (2013.01); *A61B 1/00096* (2013.01);
(Continued)

(58) Field of Classification Search
CPC ... A61B 1/00193; A61B 1/00006; A61B 1/05; A61B 1/0676; A61B 1/00183; G02B 23/2484; G02B 23/2415
(Continued)

(56) References Cited

U.S. PATENT DOCUMENTS 3,520,587 A * 7/1970 Teruo ................. A61B 1/00165
348/45
5,976,076 A * 11/1999 Kolff .................. A61B 1/00177
600/111
(Continued)

FOREIGN PATENT DOCUMENTS

JP    6-261860 A    9/1994
JP    H08-94966 A    4/1996
(Continued)

OTHER PUBLICATIONS

International Search Report dated Jan. 15, 2013 issued in PCT/JP2012/076871.
(Continued)

*Primary Examiner* — John P Leubecker
(74) *Attorney, Agent, or Firm* — Scully, Scott, Murphy & Presser, P.C.

(57) ABSTRACT

An appropriate stereoscopic image of a subject is readily acquired. Provided is a stereoscopic endoscope device including two image capture elements spaced apart from each other and disposed at a distal end of an insertion section to be inserted into a subject; an angle changing mechanism that changes a relative angle between optical axes of the image capture elements; a distance sensor that detects the distance from the image capture elements to the subject; and a controller that controls the angle changing mechanism on the basis of the distance detected by the distance sensor.

13 Claims, 22 Drawing Sheets

(51) Int. Cl.
    *A61B 1/00*     (2006.01)
    *G02B 23/24*     (2006.01)
    *A61B 5/00*     (2006.01)

(52) U.S. Cl.
    CPC .............. *A61B 1/05* (2013.01); *A61B 1/0676* (2013.01); *G02B 23/2484* (2013.01); *A61B 5/6886* (2013.01)

(58) Field of Classification Search
    USPC .................................. 600/128, 117; 348/45
    See application file for complete search history.

(56) References Cited

U.S. PATENT DOCUMENTS

| | | | | |
|---|---|---|---|---|
| 6,450,950 | B2* | 9/2002 | Irion | A61B 1/00181 600/111 |
| 2006/0009679 | A1* | 1/2006 | Ito | A61B 1/0005 600/117 |
| 2008/0027279 | A1 | 1/2008 | Abou El Kheir | |
| 2010/0163023 | A1* | 7/2010 | Singh | A61M 16/04 128/200.26 |
| 2010/0245552 | A1* | 9/2010 | Higuchi | A61B 1/00096 348/68 |
| 2010/0274089 | A1* | 10/2010 | Choi | A61B 1/00071 600/166 |
| 2011/0306832 | A1* | 12/2011 | Bassan | A61B 1/00009 600/109 |
| 2014/0055563 | A1* | 2/2014 | Jessop | H04N 13/0239 348/45 |

FOREIGN PATENT DOCUMENTS

| | | | |
|---|---|---|---|
| JP | 08116553 A | * | 5/1996 |
| JP | 11341522 A | * | 12/1999 |
| JP | 2000-308090 A | | 11/2000 |
| JP | 2005-034654 A | | 2/2005 |
| JP | 2007-532240 A | | 11/2007 |

OTHER PUBLICATIONS

Extended Supplementary European Search Report dated Jun. 15, 2015 from related European Application No. 12 83 9464.0.

* cited by examiner

FIG. 17
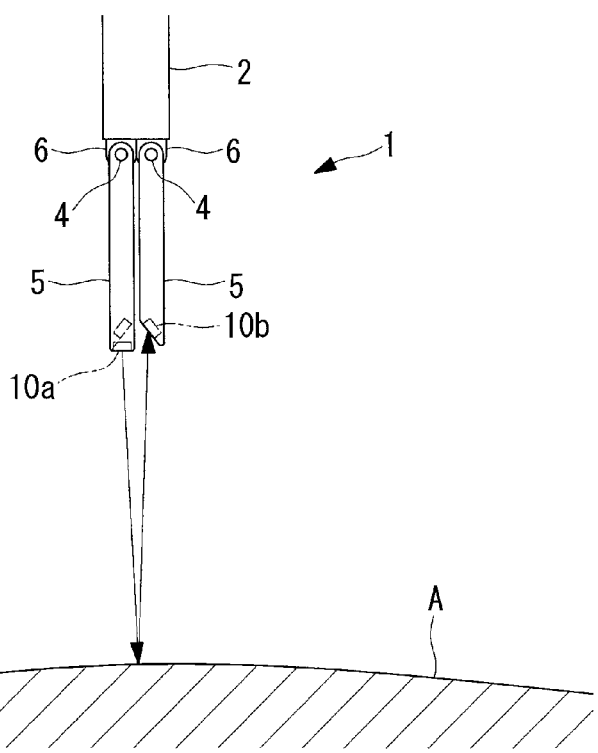
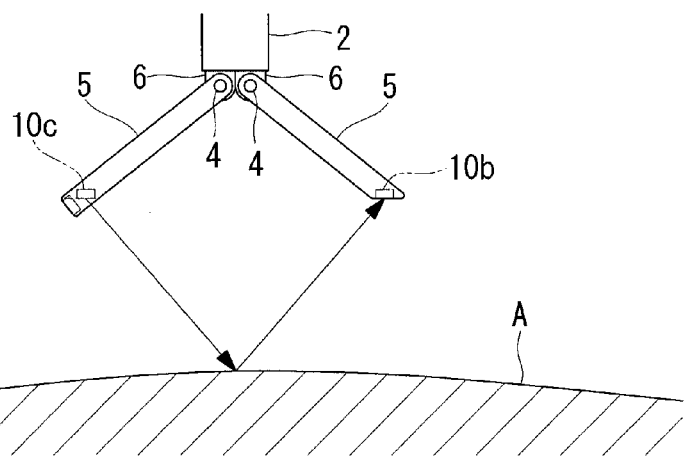

(a)

(b)

FIG. 25
(a)
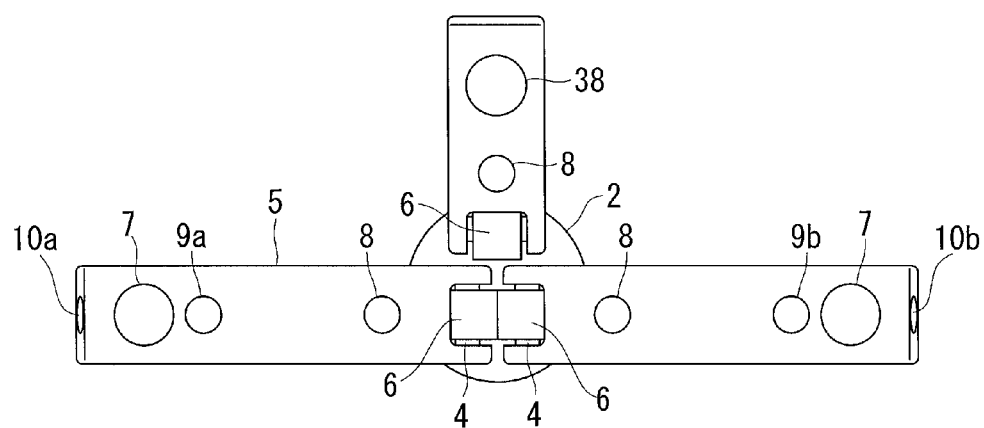
(b)
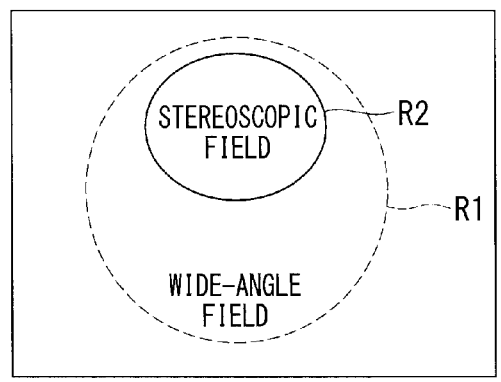

FIG. 26
(a)
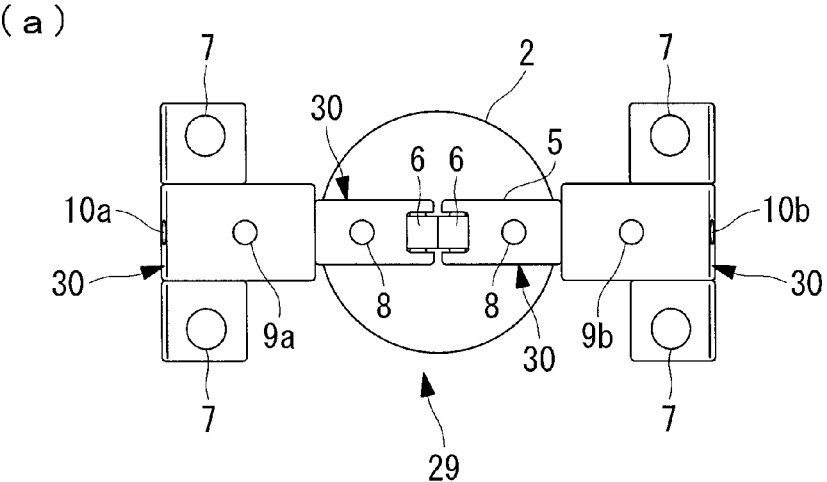
(b)
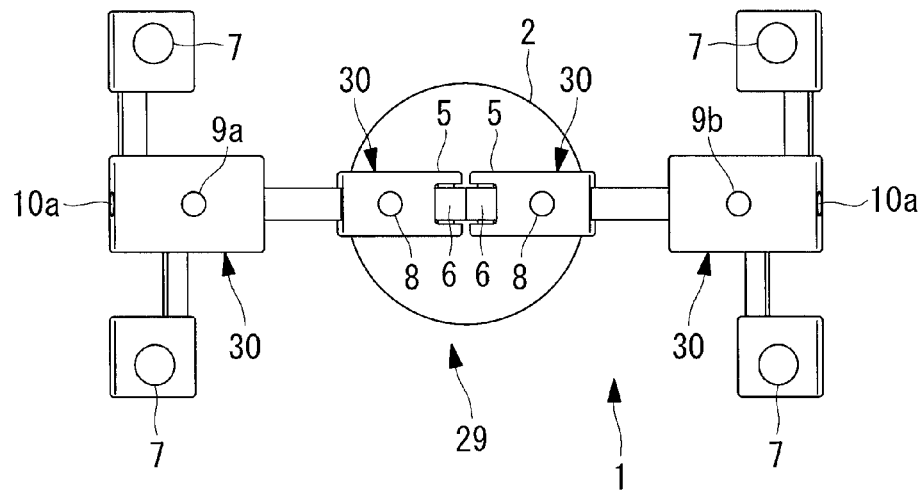

FIG. 29
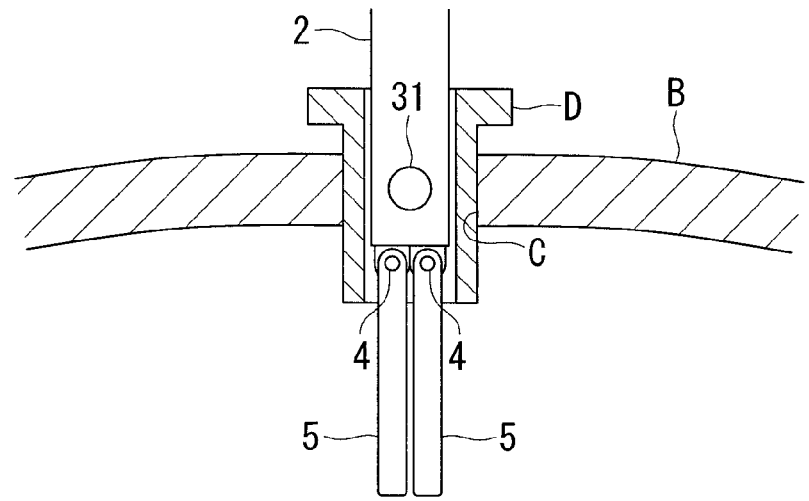
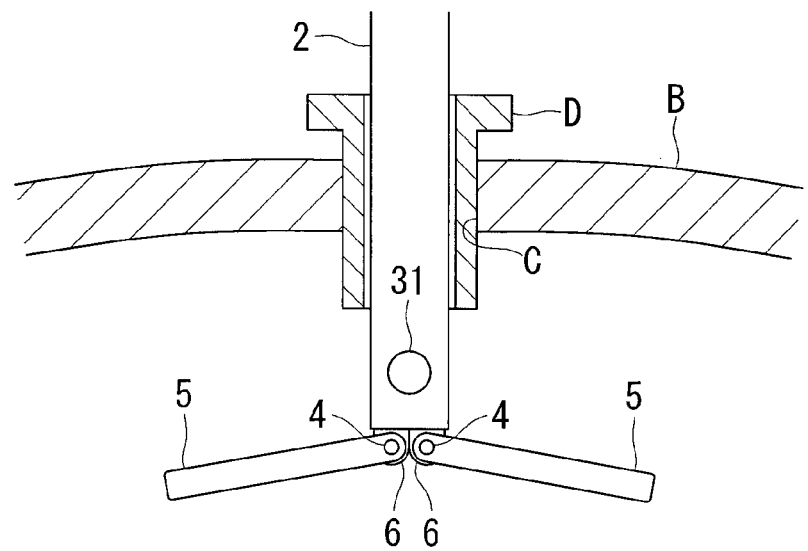

STEREOSCOPIC ENDOSCOPE DEVICE HAVING MECHANISM THAT CHANGES AN ANGLE BETWEEN OPTICAL AXES OF TWO IMAGING SENSORS

CROSS-REFERENCE TO RELATED APPLICATIONS

This is a continuation of International Application PCT/JP2012/076871, with an international filing date of Oct. 11, 2012, which is hereby incorporated by reference herein in its entirety. This application claims the benefit of Japanese Patent Application No. 2011-227099, the contents of which are incorporated herein by reference.

TECHNICAL FIELD

The present invention relates to stereoscopic endoscope devices.

BACKGROUND ART

With regard to endoscopes used in surgical operations in the related art, a technology for stereoscopically viewing a subject is known (for example, see Patent Literature 1).

In the technology disclosed in Patent Literature 1, an internal angle, which is an angle formed between intersecting optical axes of multiple image fibers disposed at a distal end of an insertion section to be inserted into a body, is adjusted by deforming the ends of the image fibers, thereby changing a stereoscopic effect of an acquired image. In the technology described in Patent Literature 1, the adjustment of the internal angle based on the deformation of the image fibers needs to be performed in a trial-and-error fashion by an observer, such as a doctor, while viewing a monitor. An appropriate stereoscopic image of a subject cannot be readily acquired.

CITATION LIST

Patent Literature

{PTL 1}
Japanese Unexamined Patent Application, Publication No. Hei 8-94966

SUMMARY OF INVENTION

The present invention is to provide a stereoscopic endoscope device that can readily acquire an appropriate stereoscopic image of a subject.

An aspect of the present invention provides a stereoscopic endoscope device including two image capture elements spaced apart from each other and disposed in an insertion section to be inserted into a subject; an angle changing mechanism that changes a relative angle between optical axes of the image capture elements; a distance sensor that detects a distance from the image capture elements to the subject; and a controller that controls the angle changing mechanism on the basis of the distance detected by the distance sensor.

BRIEF DESCRIPTION OF DRAWINGS

FIG. 17 illustrates (a) a distance detection process in the closed position, performed by the stereoscopic endoscope device provided with the distance sensors in FIG. 16, and (b) a distance detection process in the open position.

FIG. 25 illustrates a modification of the stereoscopic endoscope device in FIG. 1, and shows (a) a stereoscopic endoscope device equipped with a wide-angle image capture element in addition to the two stereoscopic image capture elements, and (b) an example of an acquired image.

FIG. 26 illustrates a modification in which the distances between a plurality of image capture elements in the stereoscopic endoscope device in FIG. 1 are adjustable, and shows (a) a state where the image capture elements are moved closer to each other, and (b) a state where the image capture elements are moved away from each other.

FIG. 29 illustrates a modification of the stereoscopic endoscope device in FIG. 1, and shows (a) a pre-inserted state of a stereoscopic endoscope device having a $CO_2$ sensor that detects whether the insertion section is inserted into the body, and (b) an inserted state thereof.

DESCRIPTION OF EMBODIMENTS

A stereoscopic endoscope device 1 according to an embodiment of the present invention will be described below with reference to the drawings.

Figure 1:
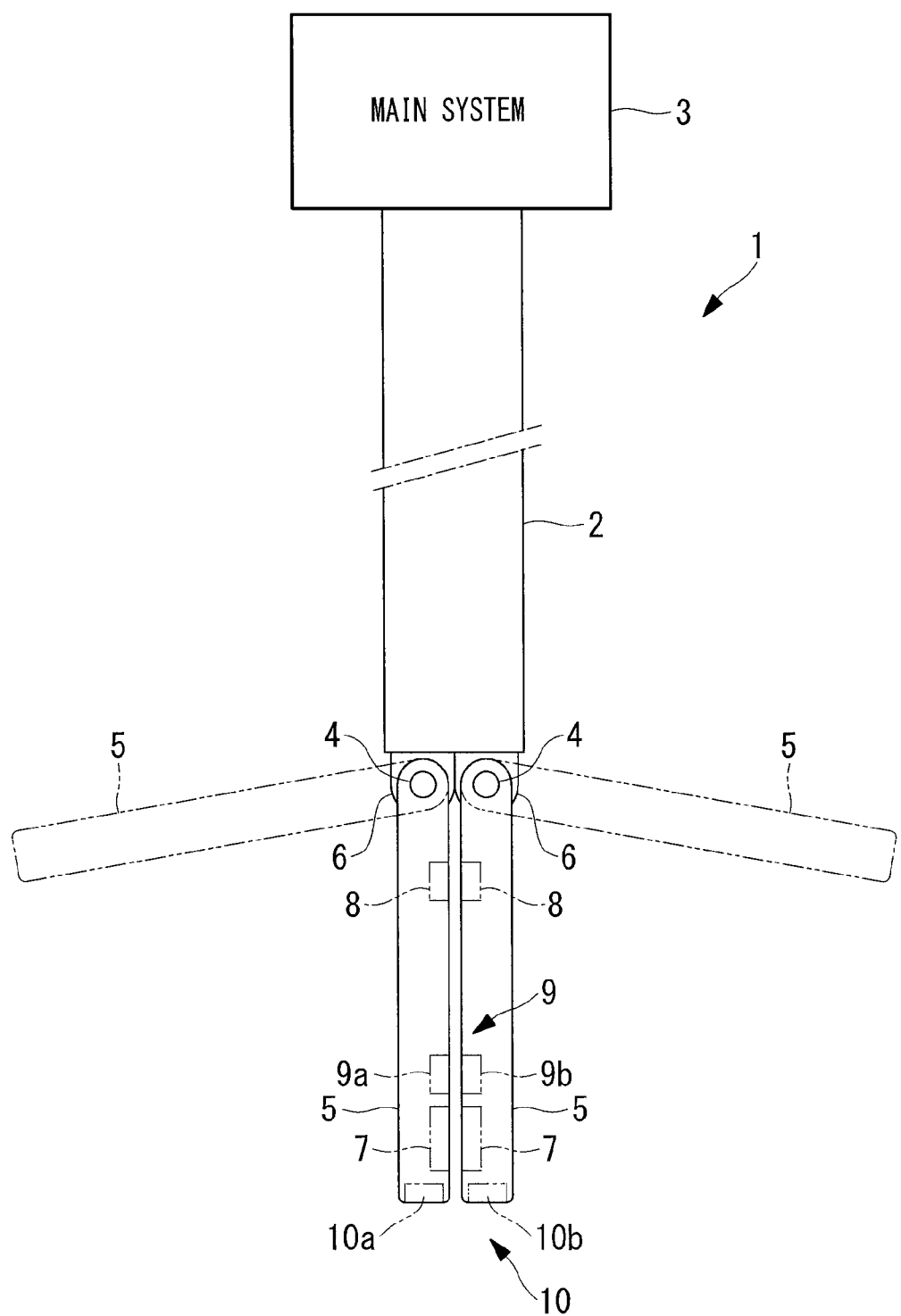
FIG. 1 illustrates the overall configuration of a stereoscopic endoscope device according to an embodiment of the present invention.
Figure 2:
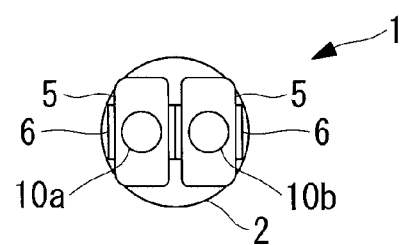
FIG. 2 is a front view illustrating a state where pivoting members of the stereoscopic endoscope device in FIG. 1 are disposed in a closed position, as viewed from the distal ends thereof.
Figure 3:
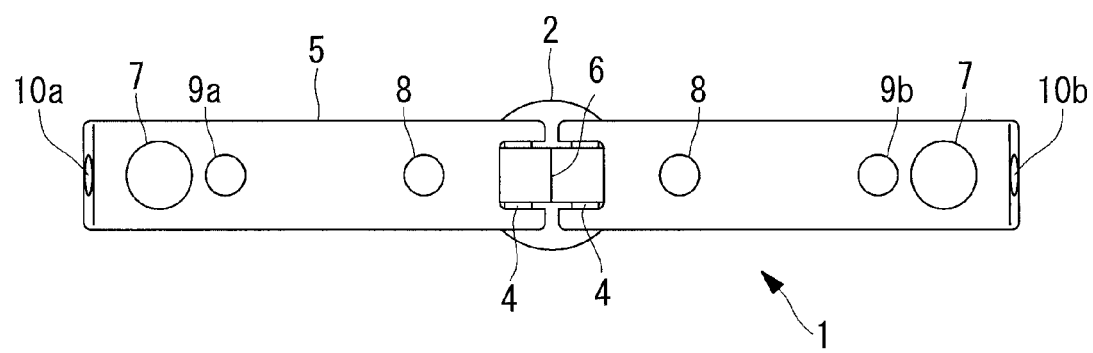
FIG. 3 is a front view illustrating a state where the pivoting members of the stereoscopic endoscope device in FIG. 1 are disposed in an open position, as viewed from the distal ends thereof.

As shown in FIGS. 1 to 3, the stereoscopic endoscope device 1 according to this embodiment includes a narrow insertion section 2 insertable into the body (i.e., a subject) of a patient, and a main system 3 connected to the insertion section 2.

The distal end of the insertion section 2 is provided with two pivoting members 5 that are pivotably supported by two shafts 4 extending parallel to a direction orthogonal to the longitudinal axis of the insertion section 2.

The base ends of the pivoting members 5 are respectively provided with rotary micro-actuators (i.e., driving sections) 6 that rotate the shafts 4.

The two rotary micro-actuators 6 synchronously rotate the shafts 4 in opposite directions so as to move the two pivoting members 5 back and forth between a closed position (indicated by solid lines in FIG. 1) in which the pivoting members 5 are disposed close to each other so as to extend along the longitudinal axis of the insertion section 2, and an open position (indicated by chain lines in FIG. 1) in which the pivoting members 5 are disposed away from each other.

Each pivoting member 5 is provided with an image capture element 7, an illumination element 8, and a distance sensor 9 that are disposed facing their counterparts in the other pivoting member 5 when the pivoting members 5 are disposed in the closed position.

The image capture elements 7 are, for example, CCDs or CMOS imagers having optical axes 7a extending orthogonally to the pivoting members 5. The illumination elements 8 are, for example, LEDs that emit illumination light in a direction intersecting the pivoting members 5.

The distance sensors 9 include, for example, a light-emitting element 9a provided in one of the pivoting members 5 and a light-receiving element 9b provided in the other pivoting member 5. Light emitted from the light-emitting element 9a is reflected at a subject A (see FIG. 5) so as to be received by the light-receiving element 9b. The quantity of light received by the light-receiving element 9b is small when the distance is long, and is large when the distance is short. Therefore, the distance from the distance sensors 9 to the subject A can be detected on the basis of the quantity of received light.

Furthermore, in this embodiment, the distal ends of the pivoting members 5 are provided with distal-end distance sensors (i.e., closed-position distance sensors) 10 that detect the distance from the subject A to the pivoting members 5 in a state where the pivoting members 5 are disposed in the closed position. Similarly to the distance sensors 9 described above, the distal-end distance sensors 10 also include a light-emitting element 10a and a light-receiving element 10b.

Figure 4:
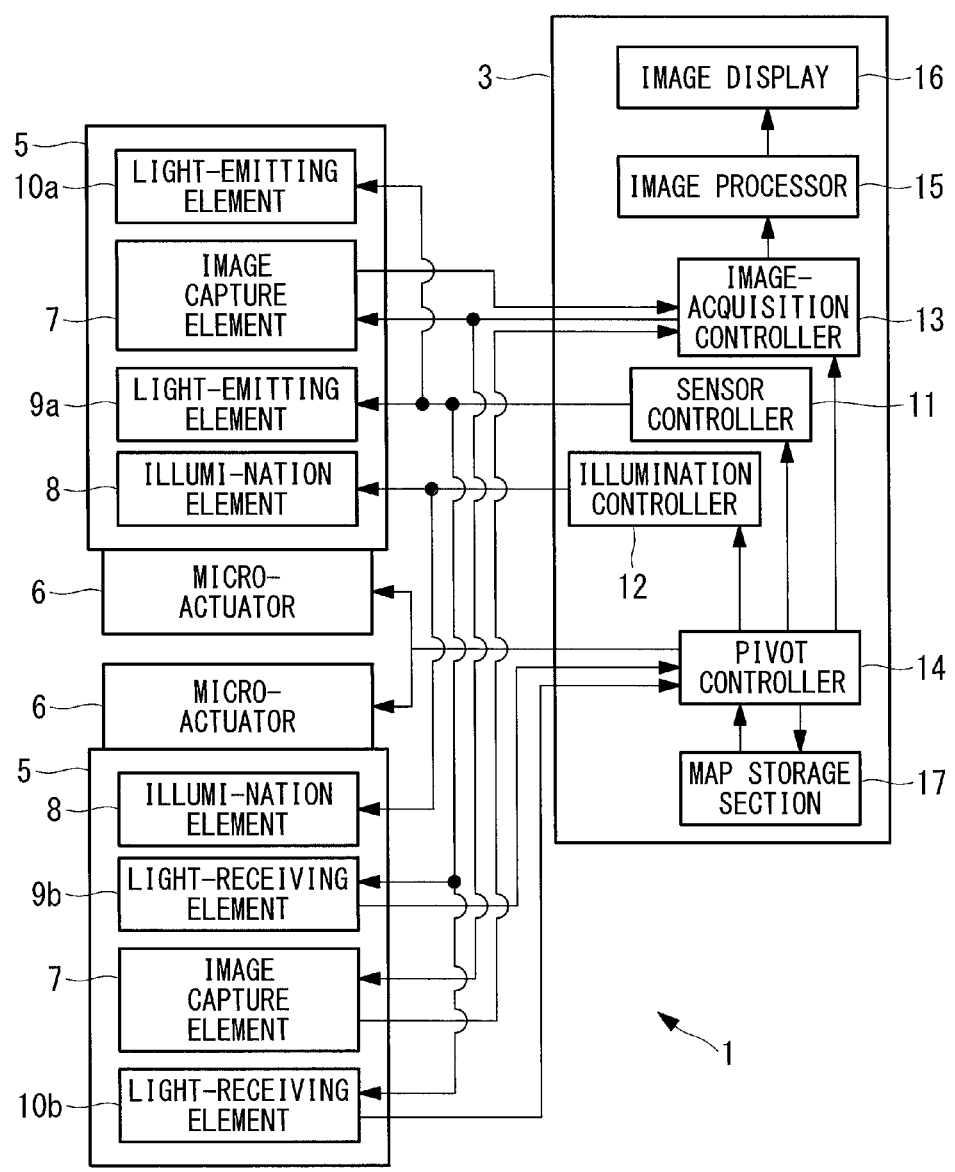
FIG. 4 is a functional block diagram of the stereoscopic endoscope device in FIG. 1.

As shown in FIG. 4, the main system 3 includes a sensor controller 11 that controls the distance sensors 9 and the distal-end distance sensors 10, an illumination controller 12 that performs on/off control of the illumination elements 8, an image-acquisition controller 13 that controls image acquisition by the image capture elements 7, a pivot controller (controller) 14 that controls the angles of the pivoting members 5, an image processor 15 that processes image signals acquired by the image capture elements 7, an image display 16 that displays the images processed by the image processor 15, and a map storage section 17 that stores a map indicating a correspondence relationship between distance and internal angle.

Figure 5:
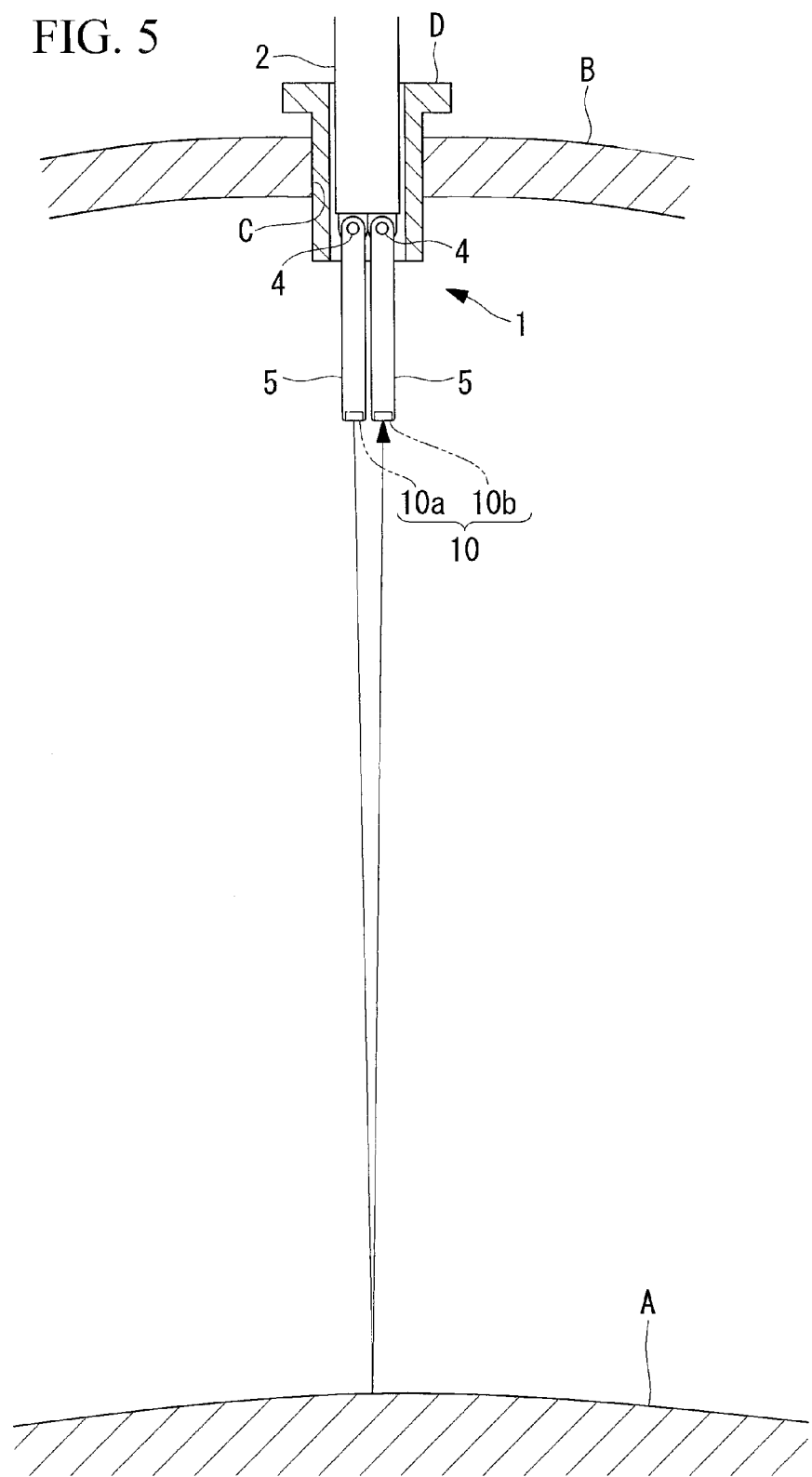
FIG. 5 illustrates a state where an insertion section of the stereoscopic endoscope device in FIG. 1 is inserted into the body while the pivoting members are disposed in the closed position.
Figure 7:
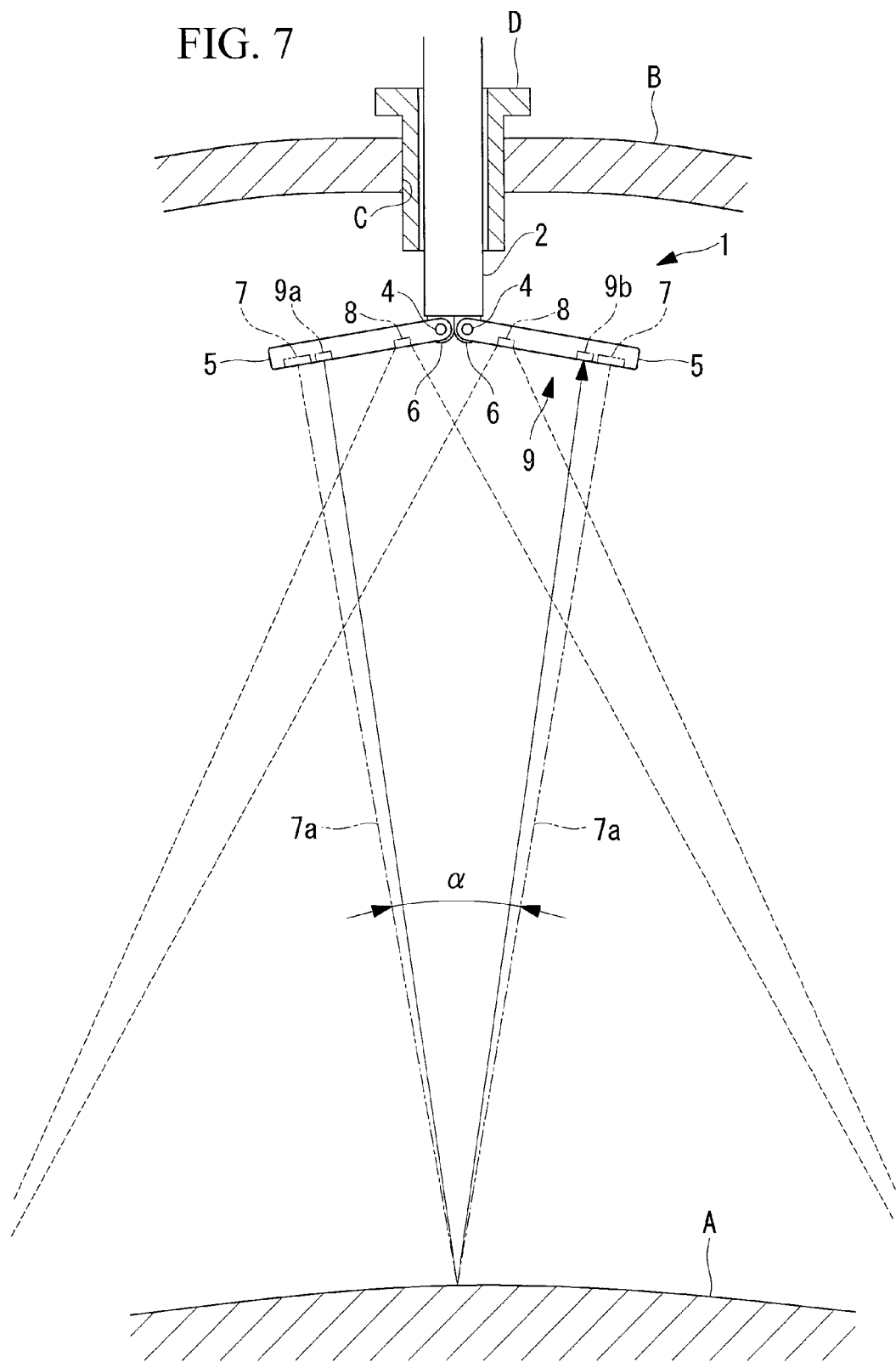
FIG. 7 illustrates a state where relatively long-range observation is performed by disposing the pivoting members in the open position from the position in FIG. 6 and activating image capture elements, etc.
Figure 8:
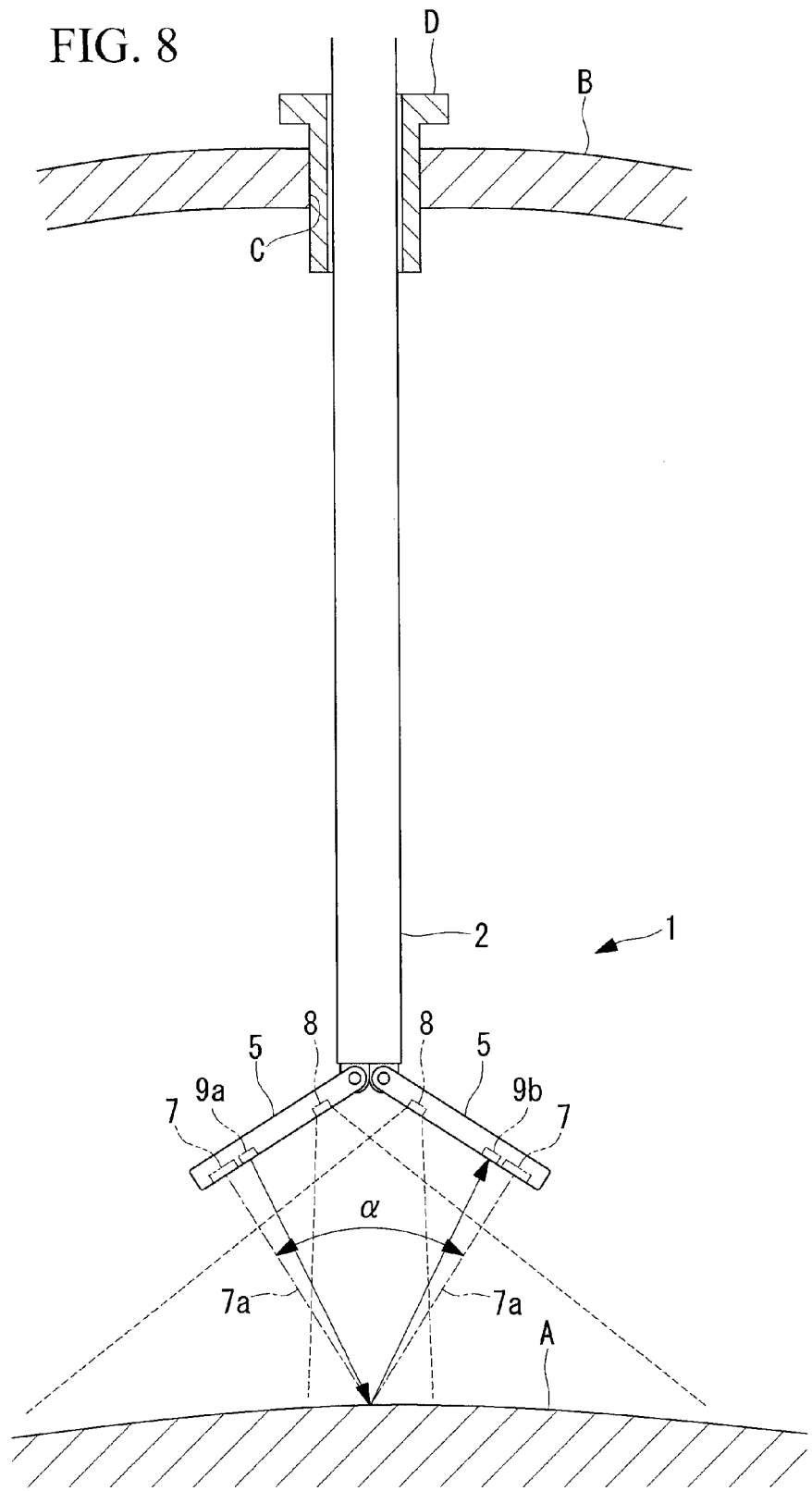
FIG. 8 illustrates a state where relatively close-range observation is performed by inserting the insertion section further into the body from the position in FIG. 7.

In an inserted state in which the pivoting members 5 are disposed in the closed position, as shown in FIG. 5, the sensor controller 11 activates the distal-end distance sensors 10. When the pivoting members 5 are disposed in the open position, as shown in FIG. 7, the sensor controller 11 activates the distance sensors 9.

Figure 6:
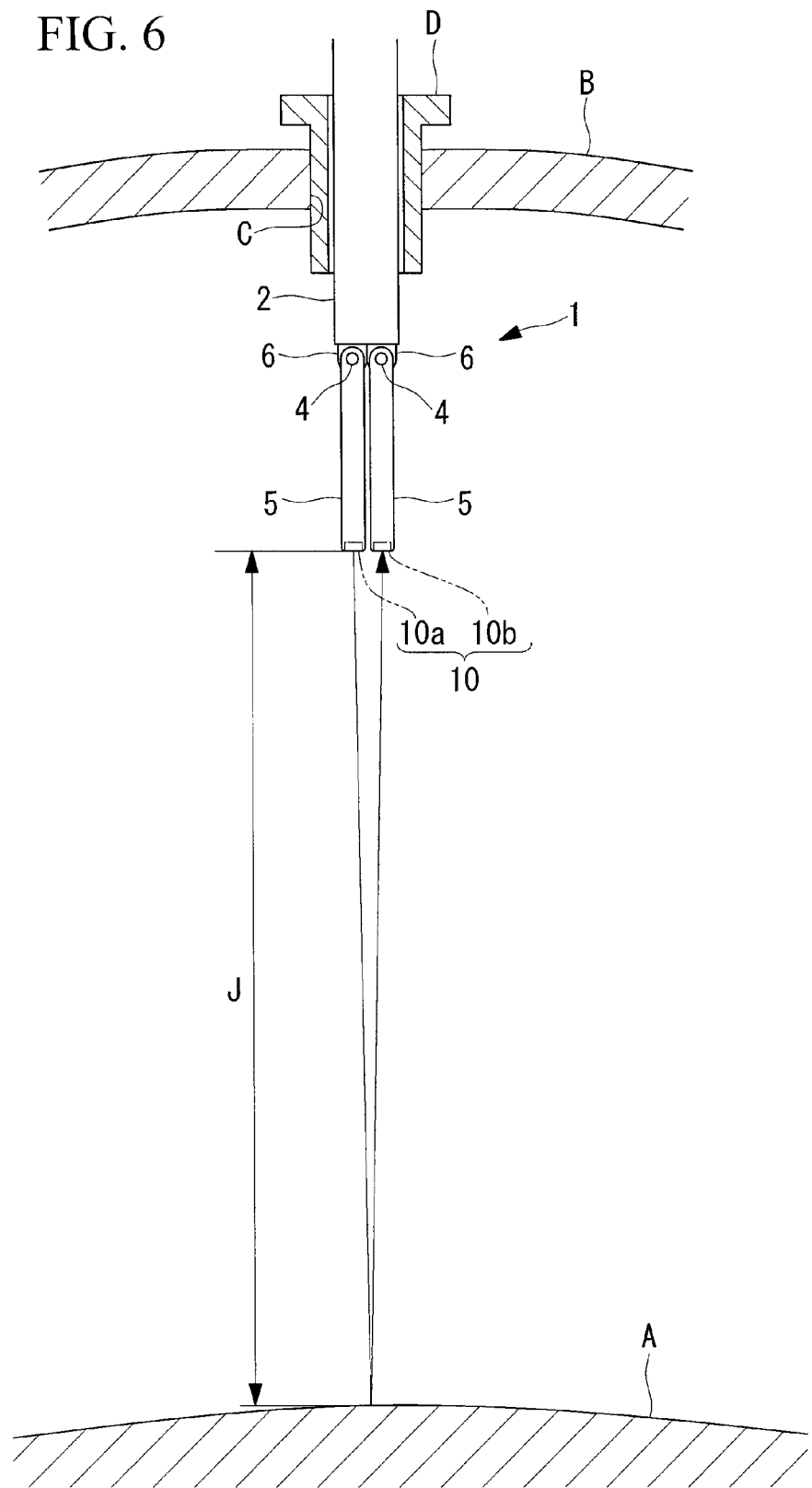
FIG. 6 illustrates a state where the insertion section is further inserted into the body from the state in FIG. 5 so that a distance d between the distal ends of the pivoting members and a subject is equal to J.

The light-receiving elements 9b and 10b respectively constituting the distance sensors 9 and the distal-end distance sensors 10 output a voltage signal according to the quantity of received light to the pivot controller 14. In the inserted state in which the pivoting members 5 are disposed in the closed position, the pivot controller 14 monitors the voltage signal from the light-receiving element 10b constituting the distal-end distance sensors 10, and activates the rotary micro-actuators 6 when the voltage signal exceeds a stored predetermined threshold value, that is, when the distance between the subject A and the distal ends of the pivoting members 5 reaches a predetermined distance J, as shown in FIG. 6. From this state, the pivoting members 5 are pivoted from the closed position to an initial open position, as shown in FIG. 7.

Furthermore, the pivot controller 14 outputs activation signals to the sensor controller 11, the illumination controller 12, and the image-acquisition controller 13 when the pivoting members 5 are pivoted to the initial open position.

The sensor controller 11, upon receiving the activation signal, drives the distance sensors 9 in place of the distal-end distance sensors 10 so as to make the distance sensors 9 detect the distance to the subject A.

The illumination controller 12, upon receiving the activation signal, activates the illumination elements 8, and the image-acquisition controller 13, upon receiving the activation signal, activates the image capture elements 7.

When the pivot controller 14 receives the voltage signal from the light-receiving element 9b constituting the distance sensors 9, the pivot controller 14 calculates a distance d corresponding to the received voltage signal, retrieves an internal angle α corresponding to the distance d from the map stored in the map storage section 17, and drives the rotary micro-actuators 6 so that the retrieved internal angle α is achieved.

Figure 9:
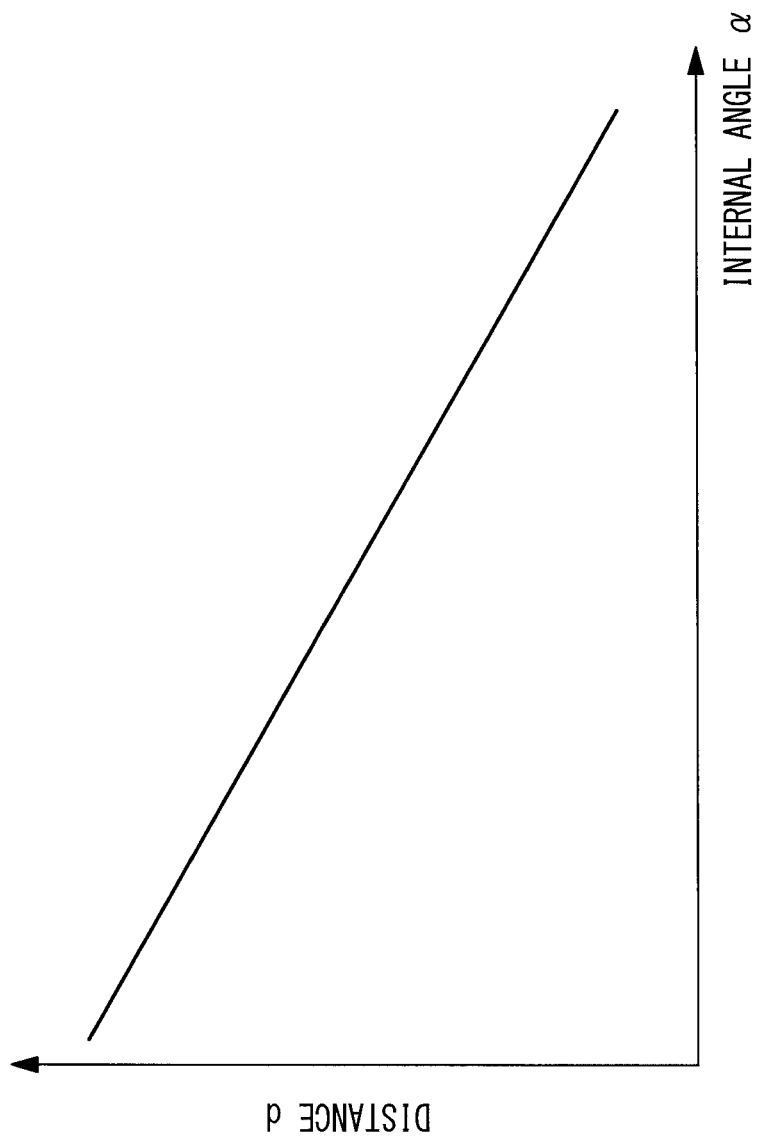
FIG. 9 is a graph illustrating an example of a map stored in a map storage section in FIG. 4 and indicating the relationship between distance d and internal angle $\alpha$.

For example, the map stored in the map storage section 17 indicates that the distance d and the internal angle α have a linear relationship, as shown in FIG. 9. This relationship indicates that the optical axes 7a of the two image capture elements 7 intersect at a position on the surface of the subject A disposed away from the image capture elements 7 by a distance d and form a corresponding internal angle.

By using the internal angle α retrieved from the map on the basis of the distance d detected by the distance sensors 9, the pivot controller 14 calculates the angles of the pivoting members 5 at which the internal angle α is achieved, and performs control so as to rotate the shafts 4 of the rotary micro-actuators 6 to the calculated angles.

The operation of the stereoscopic endoscope device 1 according to this embodiment, having the above-described configuration, will be described below.

Figure 10:
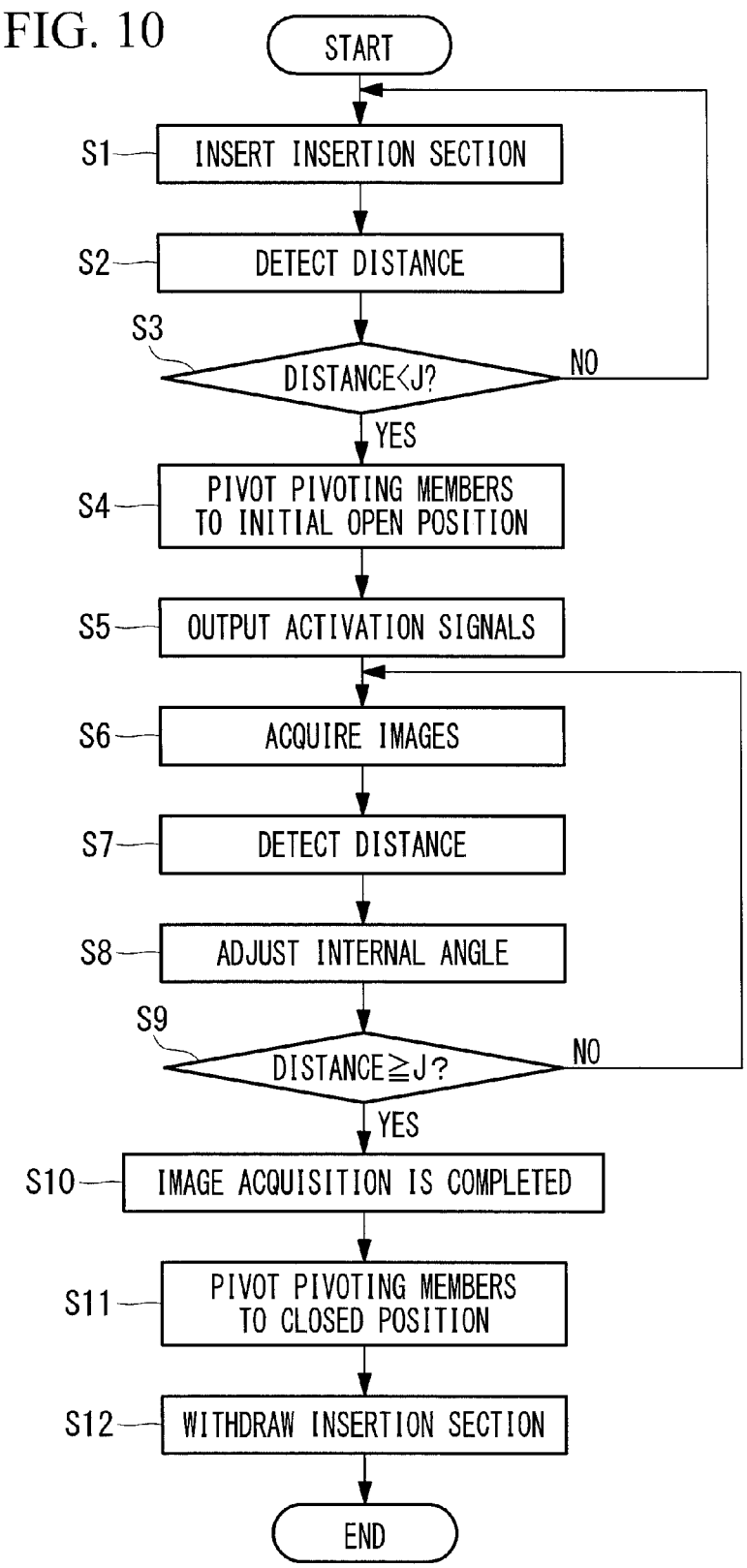
FIG. 10 is a flowchart for explaining an observation process using the stereoscopic endoscope device in FIG. 1.

Referring to FIG. 10, in order to observe the subject A inside the body by using the stereoscopic endoscope device 1 according to this embodiment, the rotary micro-actuators 6 are activated so as to dispose the two pivoting members 5 in the closed position indicated by the solid lines in FIG. 1. In this state, the insertion section 2 is inserted into the space inside the body via a through-hole in a trocar D disposed within an opening C extending through body surface tissue B, starting from the distal ends of the pivoting members 5, as shown in FIG. 5 (step S1).

In this case, the sensor controller 11 activates the light-emitting element 10a and the light-receiving element 10b of the distal-end distance sensors 10 (step S2). Thus, as shown in FIG. 5, a voltage signal indicating the quantity of light received by the light-receiving element 10b after being emitted from the light-emitting element 10a and reflected at the subject A within the body is input to the pivot controller 14, thereby determining the distance d (step S3). As shown in FIG. 6, if the distance d detected by the distal-end distance sensors 10 is smaller than the predetermined distance J, the pivot controller 14 activates the rotary micro-actuators 6 at that position so as to cause the two pivoting members 5 to pivot to the predetermined initial open position (step S4).

Furthermore, as the pivot controller 14 causes the pivoting members 5 to pivot to the initial open position, the pivot controller 14 simultaneously outputs activation signals to the sensor controller 11, the illumination controller 12, and the image-acquisition controller 13 (step S5). The sensor controller 11, upon receiving the activation signal, stops the previously-activated distal-end distance sensors 10 and activates the light-emitting element 9a and the light-receiving element 9b of the distance sensors 9.

The illumination controller 12, upon receiving the activation signal, activates the illumination elements 8 so that illumination light is radiated onto the subject A. Furthermore, the image-acquisition controller 13, upon receiving the activation signal, activates the two image capture elements 7 so that two kinds of images of the subject A captured from left and right directions are acquired (step S6).

The voltage signal corresponding to the quantity of light received by the light-receiving element 9b of the distance sensors 9 is transmitted to the pivot controller 14, where a distance d is calculated (step S7). Then, the pivot controller 14 uses the calculated distance d to retrieve a corresponding internal angle α within the map stored in the map storage section 17 and calculates the angles of the pivoting members 5 for achieving the retrieved internal angle α. The pivot controller 14 operates the rotary micro-actuators 6 until the pivoting members 5 are set to the calculated angles (step S8).

The map stores distances d at which the optical axes 7a of the two image capture elements 7 meet on the surface of the subject A in correspondence with internal angles α. Therefore, by pivoting the pivoting members 5 so that the internal angle α corresponding to the detected distance d is achieved, two kinds of images of the subject A viewed from the left and right directions can be acquired in a state where the optical axes 7a of the two image capture elements 7 constantly meet on the surface of the subject A.

Then, the image acquisition process, the distance-d detection process, and the internal-angle-α adjustment process from step S6 to step S8 are repeated until the insertion section 2 is withdrawn such that the distance d detected by the distance sensors 9 becomes larger than or equal to the predetermined distance J (step S9). Subsequently, when the insertion section 2 is withdrawn such that the detected distance d is larger than or equal to the predetermined distance J, the pivot controller 14 outputs a signal indicating the completion of the image acquisition to the illumination controller 12 and the image-acquisition controller 13 (step S10).

Consequently, the illumination elements 8 and the image capture elements 7 stop operating, thereby completing the image acquisition. Furthermore, the pivot controller 14 subsequently operates the rotary micro-actuators 6 so as to dispose the two pivoting members 5 in the closed position (step S11), and commands the sensor controller 11 to stop the distance sensors 9 and activate the distal-end distance sensors 10. Thus, the insertion section 2 and the pivoting members 5 can be withdrawn from the body via the trocar D (step S12).

With the stereoscopic endoscope device 1 according to this embodiment, the internal angle α is adjusted by pivoting the pivoting members 5 on the basis of the distance d detected by the distance sensors 9, so that the intersecting point of the optical axes 7a of the two image capture elements 7 always coincides with the surface of the subject A. This is advantageous in that the subject A can be observed with an appropriate stereoscopic effect without the observer, such as a doctor, having to adjust the internal angle α in a trial-and-error fashion while viewing a monitor.

Figure 11:
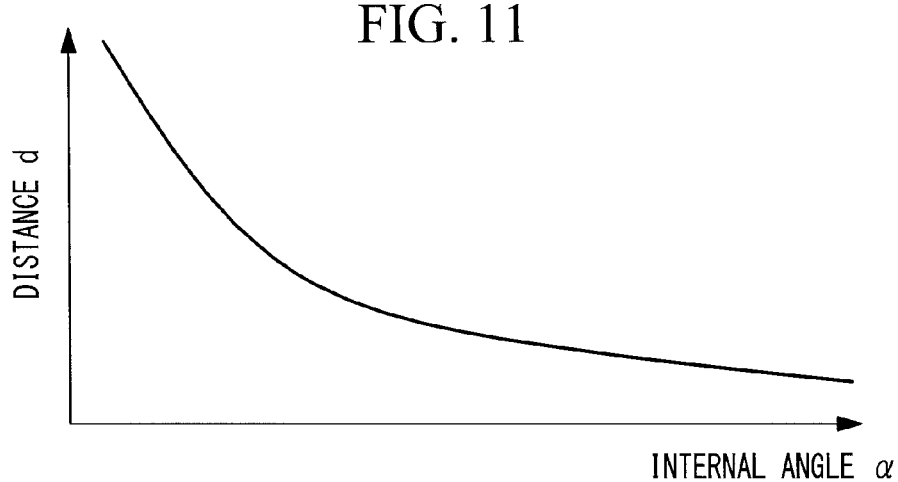
FIG. 11 is a graph illustrating a first modification of the map in FIG. 9.

Although the internal angle α changes linearly relative to the detected distance d in this embodiment, the internal angle α may alternatively change in a curved fashion, as shown in FIG. 11.

Figure 12:
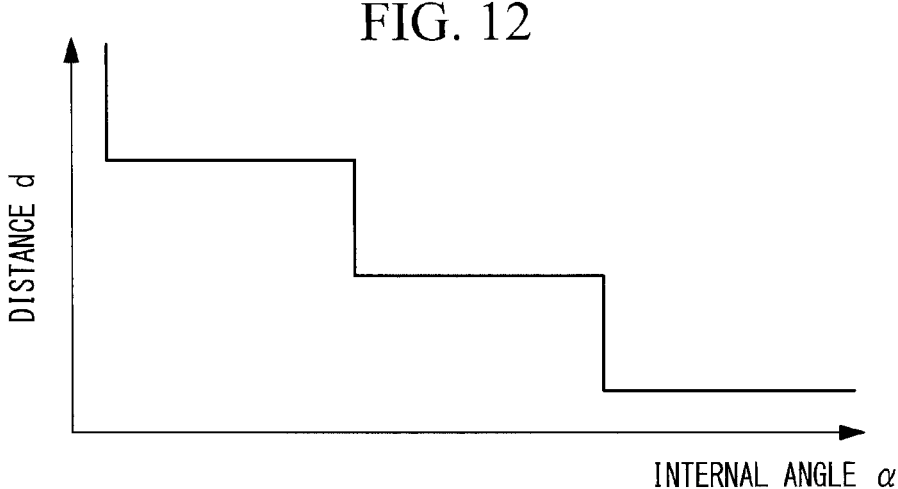
FIG. 12 is a graph illustrating a second modification of the map in FIG. 9.

Furthermore, as shown in FIG. 12, the internal angle α may change in a stepwise fashion relative to the distance d.

Accordingly, even in a case where the distance d between the insertion section 2 and the subject A changes frequently, the stereoscopic effect of images displayed on the image display 16 is prevented from changing frequently since the internal angle α changes in a stepwise fashion, thereby advantageously reducing unpleasantness during the observation.

Figure 13:
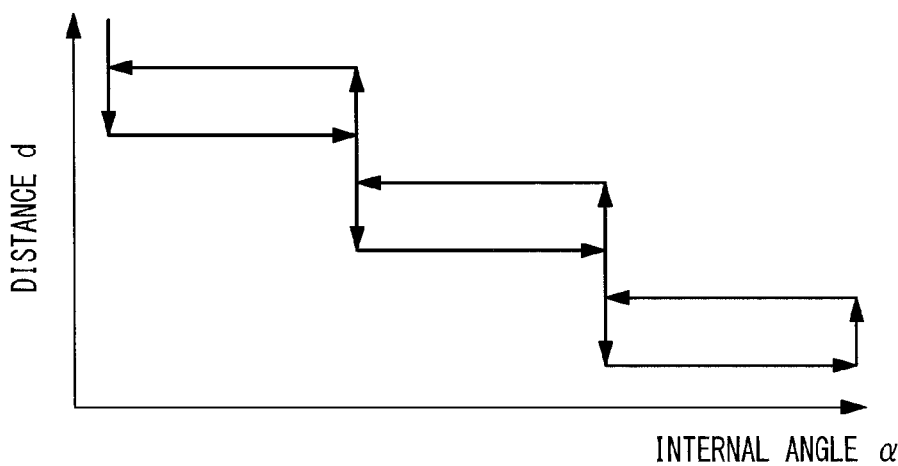
FIG. 13 is a graph illustrating a third modification of the map in FIG. 9.

In the case where the internal angle α changes in a stepwise fashion relative to the distance d, a map indicating that the internal angle α changes relative to different distances d between when the insertion section 2 is moved toward the subject A and when the insertion section 2 is moved away from the subject A may be provided, as shown in FIG. 13. Accordingly, when the insertion section 2 is moved back and forth frequently, the internal angle α is prevented from changing frequently, thereby reducing unpleasantness during the observation.

Furthermore, a plurality of maps indicating different relationships between the distance d and the internal angle α may be stored in the map storage section 17. In that case, a map selecting section (not shown) to be used by the observer for selecting an appropriate map may be provided. Accordingly, the observer can select an appropriate map in accordance with the type of subject A, whereby stereoscopic observation can be performed with reduced unpleasantness caused by a change in the internal angle α.

Figure 14:
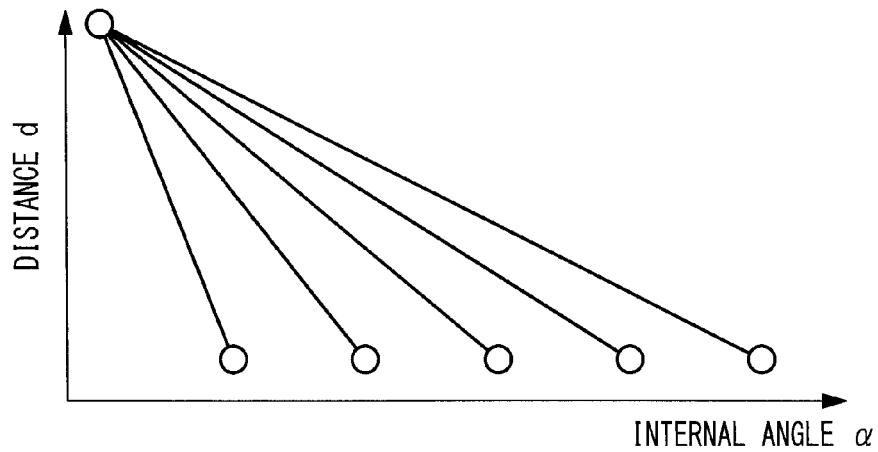
FIG. 14 is a graph illustrating a fourth modification of the map in FIG. 9.

For example, as shown in FIG. 14, a plurality of maps in which the internal angle α varies therebetween as the distance between the insertion section 2 and the subject A decreases may be stored. Accordingly, when performing a precise procedure by observing a magnified image, an observation option based on an optimal stereoscopic image can be selected in accordance with the procedure. In this case, it is preferable that the internal angle α be selectable within a range between 1° and 10°. Thus, unpleasantness, fatigue, dizziness, etc. caused by performing the observation at an excessive internal angle α can be reduced.

Figure 15:
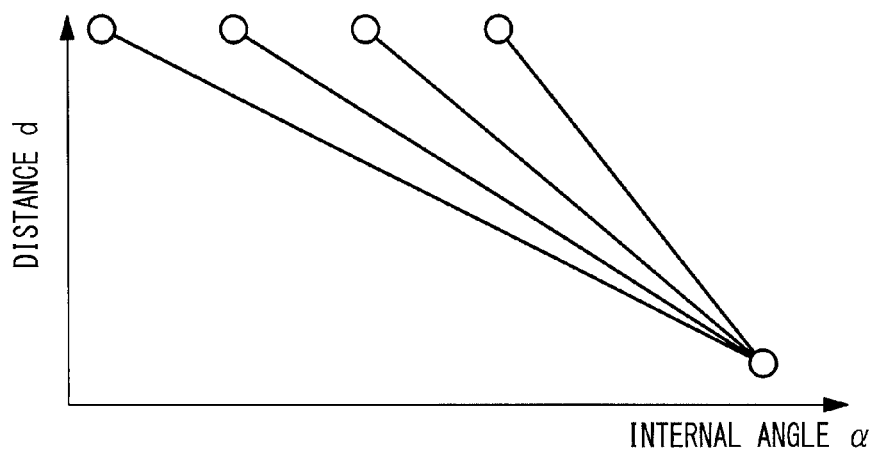
FIG. 15 is a graph illustrating a fifth modification of the map in FIG. 9.

Furthermore, as shown in FIG. 15, a plurality of maps in which the internal angle α varies therebetween as the distance between the insertion section and the subject increases may be stored. Accordingly, when performing a macro-procedure by observing a wide region, an observation option based on an optimal stereoscopic image can be selected in accordance with the procedure. In this case, it is preferable that the internal angle α be selectable within a range between 0° and 10°. Thus, unpleasantness, fatigue, dizziness, etc. caused by performing the observation at an excessive internal angle α can be reduced.

Furthermore, a plurality of maps with different changing patterns relative to the distance d may be stored. For example, two or more maps shown in FIGS. 11 to 15 may be stored.

Figure 16:
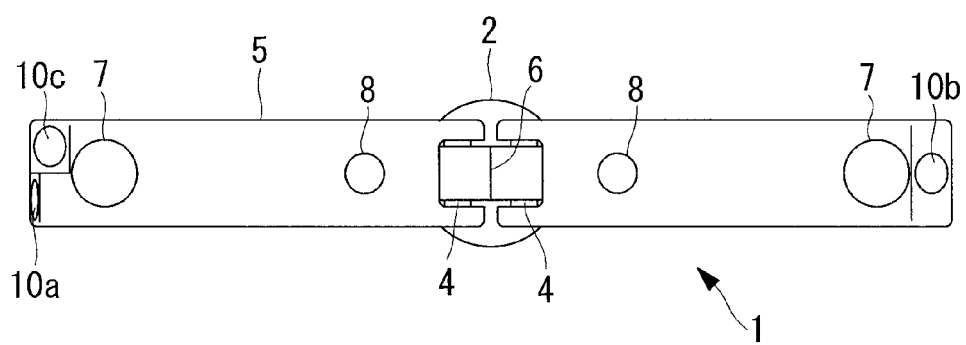
FIG. 16 is a front view illustrating a modification of distance sensors provided at the distal ends of the pivoting members of the stereoscopic endoscope device in FIG. 1.

In this embodiment, the sensors that detect the distance d to the subject A include the distal-end distance sensors 10 that are provided at the distal ends of the pivoting members 5 and are activated when the pivoting members 5 are disposed in the closed position, and the distance sensors 9 that are provided at the opposing surfaces of the two pivoting members and are activated when the pivoting members 5 are disposed in the open position. Alternatively, as shown in FIGS. 16 and 17, two light-emitting elements 10a and 10c that emit light having directional properties in different directions may be disposed at the distal end of one of the pivoting members 5, whereas the light-receiving element 10b disposed at the distal end of the other pivoting member 5 may be shared by the two light-emitting elements.

Specifically, as shown in FIG. 17(*a*), when the insertion section 2 is to be inserted into the body, the light-emitting element 10a provided at the distal end of one of the pivoting members 5 disposed in the closed position emits light in a direction along the longitudinal direction of the pivoting member 5, and the light-receiving element 10b detects reflected light from the subject A. On the other hand, as shown in FIG. 17(*b*), when the pivoting members 5 are disposed in the open position, the light-emitting element 10c provided at the distal end of one of the pivoting members 5 disposed in the open position emits light in a direction intersecting the longitudinal direction of the pivoting member 5, and the light-receiving element 10b detects reflected light from the subject A. Consequently, the number of distance sensors is reduced, thereby achieving a simplified and thinner structure.

Figure 18:
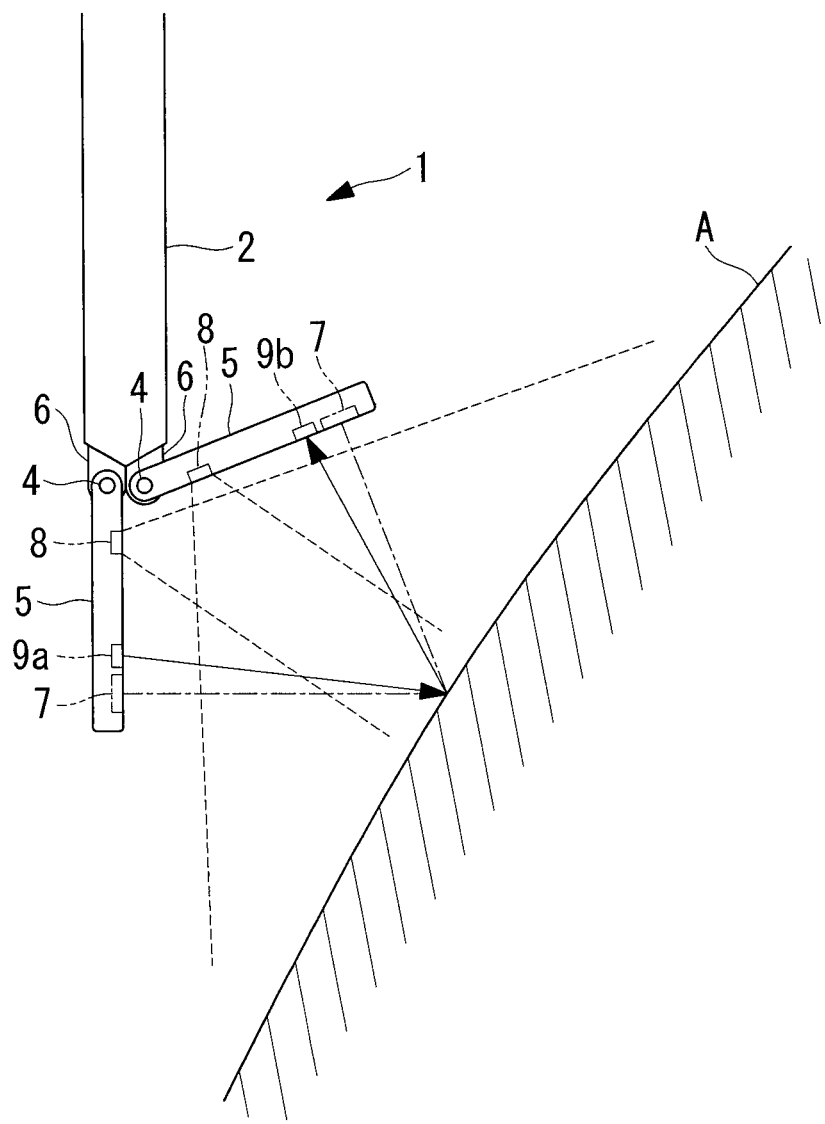
FIG. 18 illustrates a modification in which the pivoting members of the stereoscopic endoscope device in FIG. 1 are independently driven.

In this embodiment, the two pivoting members 5 synchronously pivot by the same angle in opposite directions. Alternatively, the pivoting members 5 may pivot independently of each other by different angles, as shown in FIG. 18. Accordingly, not only can a subject A disposed in front of the insertion section 2 in the longitudinal direction thereof be directly observed from the front, as shown in FIG. 7, but a subject A disposed at an angle relative to the longitudinal direction can be observed from an angle or from the side, as shown in FIG. 18. Although FIG. 18 shows a case where only one of the pivoting members 5 is pivoted, both pivoting members 5 may be pivoted by different angles or may be pivoted in the same direction.

Figure 19:
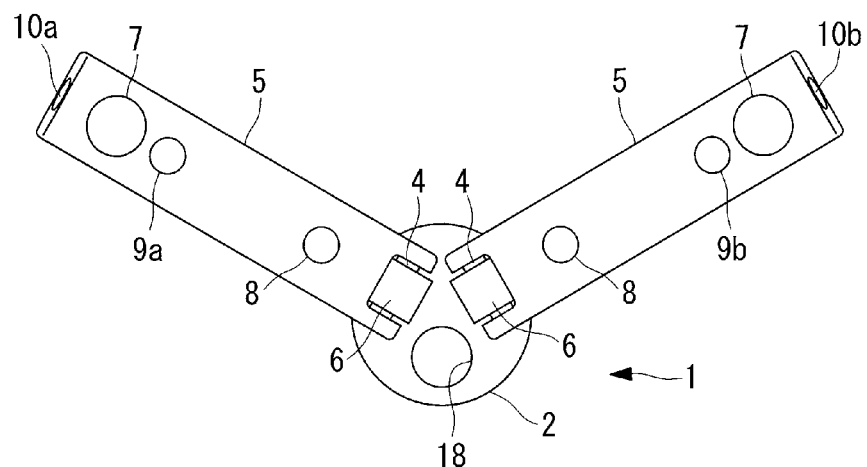
FIG. 19 is a front view illustrating a modification in which shafts that cause the two pivoting members of the stereoscopic endoscope device in FIG. 1 to pivot are disposed so as to intersect each other.

Furthermore, although the two pivoting members 5 are pivotable in opposite directions around the shafts 4 that are parallel to each other in this embodiment, the pivoting members 5 may alternatively be pivotable around the shafts 4 that intersect each other, as shown in FIG. 19.

Accordingly, in a case where the insertion section 2 is provided with a forceps channel 18, a treatment tool 19 (see FIG. 20) extending forward from the insertion section 2 via the forceps channel 18 can be disposed outside a plane including the optical axes 7a of the two image capture elements 7.

Figure 20:
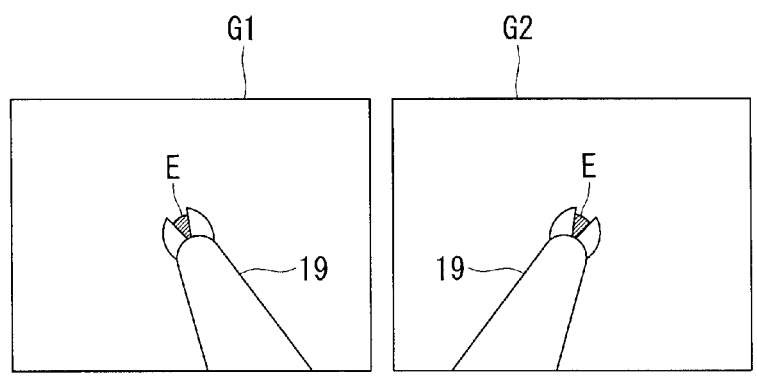
FIG. 20 illustrates example images acquired during treatment performed by using a treatment tool inserted through a forceps channel in the stereoscopic endoscope device in FIG. 19.

As a result, the treatment tool 19 within left and right images G1 and G2 acquired by the two image capture elements 7 extends from the lower edge (or the upper edge) of each image, as shown in FIG. 20, which is advantageous in that the left and right images G1 and G2 can be readily fused to form a stereoscopic image. In the drawing, reference character E denotes a treated site.

Figure 21:
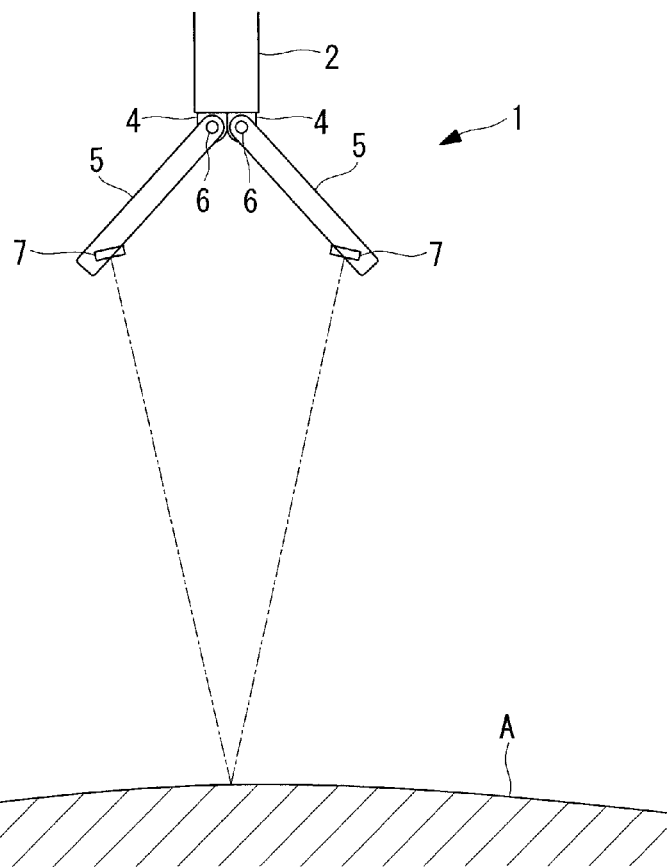
FIG. 21 illustrates a modification in which the image capture elements provided in the two pivoting members of the stereoscopic endoscope device in FIG. 1 are pivoted relative to the pivoting members, and shows (a) a state where relatively long-range observation is performed, and (b) a state where relatively close-range observation is performed.

Although the internal angle α decreases as the pivoting angles of the pivoting members 5 increase in this embodiment, the internal angle α may alternatively increase as the pivoting angles of the pivoting members 5 increase, as shown in FIG. 21. Accordingly, when the subject A is disposed at a distant position, as shown in FIG. 21(*a*), the distance between the two image capture elements 7 may be reduced by pivoting the two pivoting members 5 by small angles. When the subject A is disposed at a close position, as shown in FIG. 21(*b*), the distance between the two image capture elements 7 may be increased by pivoting the two pivoting members 5 by large angles.

Specifically, the internal angle α increases with decreasing distance from the subject A, and the internal angle α decreases with increasing distance to the subject A, whereby observation with a more appropriate stereoscopic effect can be advantageously performed. Furthermore, when observing the subject A disposed at a close position, the pivoting members 5 can be widely spread apart from each other so that the distal ends of the pivoting members 5 can be disposed away from the subject A, thereby preventing interference between the pivoting members 5 and the subject A.

In this case, image-capture-element pivoting mechanisms 20 that cause the image capture elements 7 to pivot relative to the pivoting members 5 in the pivoting direction of the pivoting members 5 may be provided.

Figure 22:
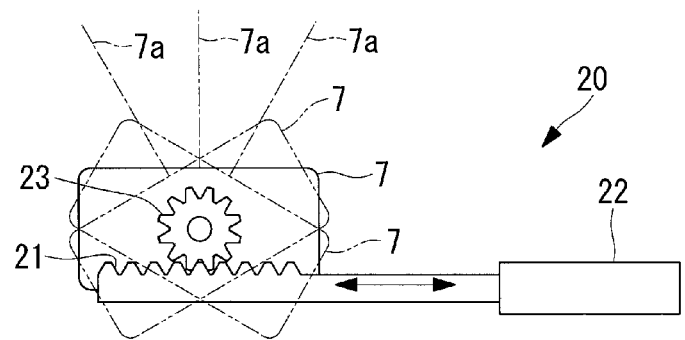
FIG. 22 illustrates an example of mechanisms for causing the image capture elements in FIG. 21 to pivot.

As shown in FIG. 22, each image-capture-element pivoting mechanism 20 may include, for example, a rack gear 21 that is movable in a reciprocating manner in the longitudinal direction of the corresponding pivoting member 5, a micro-actuator 22 that moves the rack gear 21 in a reciprocating manner, and a pinion gear 23 that is provided on the image capture element 7 and meshes with the rack gear 21.

Figure 23:
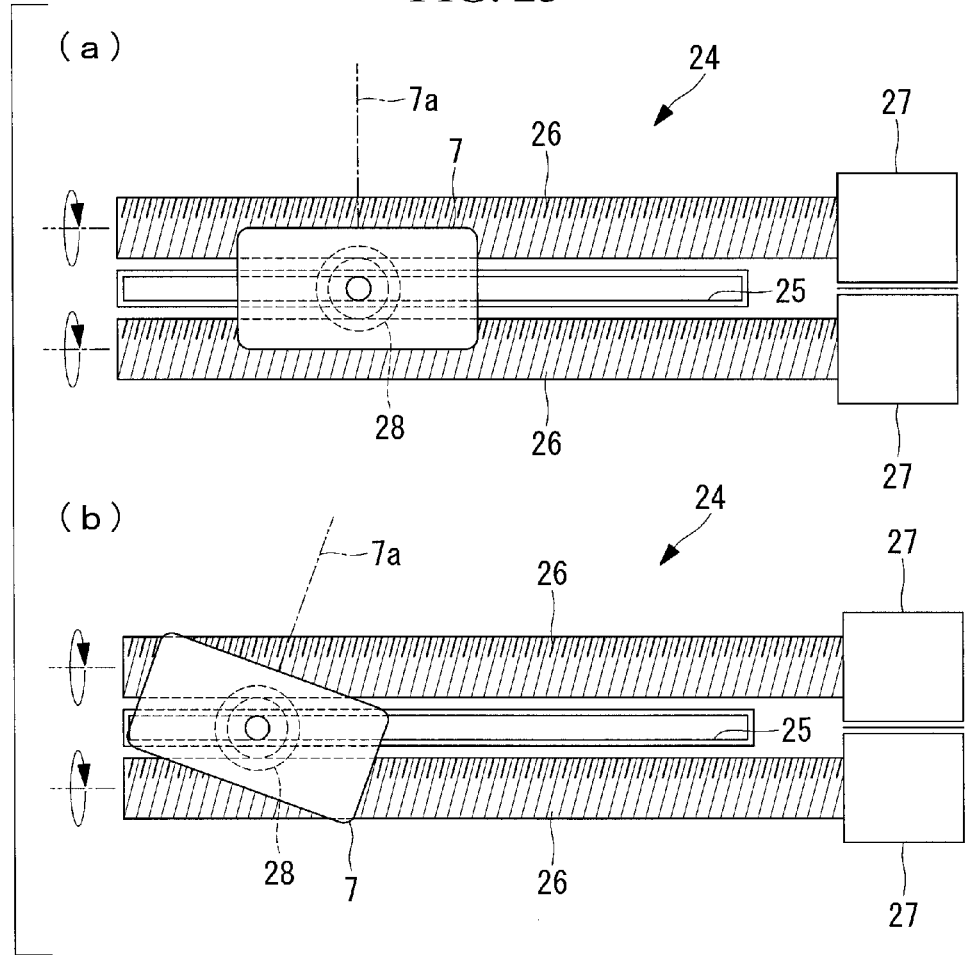
FIG. 23 illustrates an example of translation mechanisms that cause the image capture elements provided in the two pivoting members of the stereoscopic endoscope device in FIG. 1 to pivot while moving the image capture elements in the longitudinal direction of the pivoting members, and shows (a) a state where the optical axes of the image capture elements are orthogonal to the longitudinal direction of the pivoting members, and (b) a state where the image capture elements are moved toward the distal ends of the pivoting members, and the optical axes thereof are tilted inwardly relative to the direction orthogonal to the longitudinal direction of the pivoting members.

Furthermore, in addition to the adjustment of the distance between the image capture elements 7 by the pivoting of the pivoting members 5, translation mechanisms 24 that move the image capture elements 7 in the longitudinal direction of the pivoting members 5 may be provided, as shown in FIG. 23.

As shown in FIG. 23(a), each translation mechanism 24 may include a linear guide 25 that guides the movement of the corresponding image capture element 7, two feed screws 26 spaced apart from each other and extending parallel to the linear guide 25, micro-motors 27 that rotate the feed screws 26 about the axes thereof, and a pinion gear 28 that is fixed to the image capture element 7 and meshes simultaneously with the two feed screws 26.

By rotating the two feed screws 26 in the same rotational direction at slightly different rotation speeds, the image capture element 7 can be pivoted while being moved in the longitudinal direction of the pivoting member 5 along the linear guide 25, as shown in FIG. 23(b). Accordingly, when observing the subject A disposed at a close position, the image capture elements 7 are moved toward the distal ends of the pivoting members 5 so as to increase the distance therebetween, and the image capture elements 7 are inwardly pivoted, thereby achieving a larger internal angle α. On the other hand, when observing the subject A disposed at a distant position, the image capture elements 7 are moved toward the base ends of the pivoting members 5 so as to decrease the distance therebetween, and the image capture elements 7 are outwardly pivoted, thereby achieving a smaller internal angle α.

As an alternative to this embodiment in which the image capture elements 7 are pivoted relative to the pivoting members 5 by rotating the two feed screws 26 at slightly different rotation speeds, the two feed screws 26 may be rotated at exactly the same rotation speed. Accordingly, the image capture elements 7 can be moved linearly in the longitudinal direction of the pivoting members 5 without being pivoted relative to the pivoting members 5.

Figure 24:
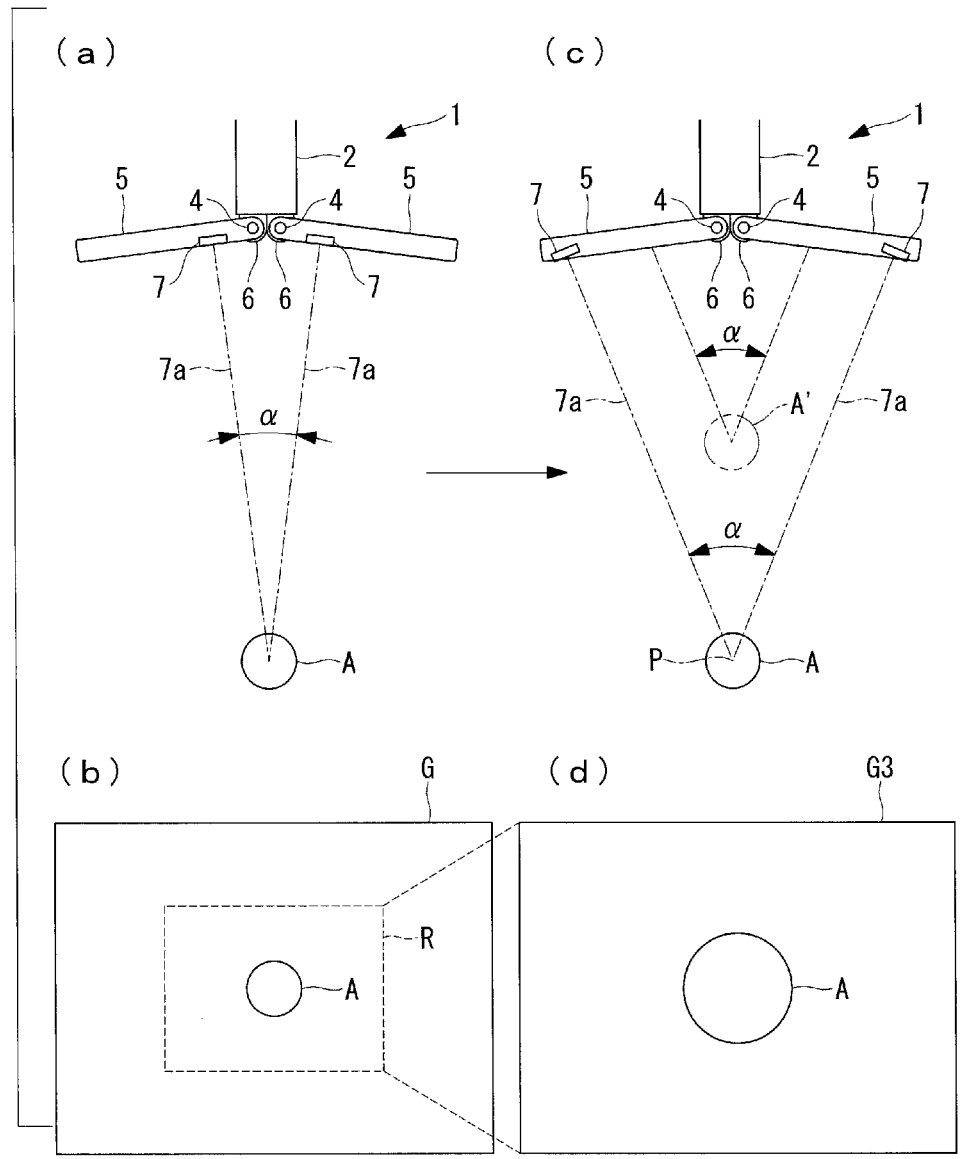
FIG. 24 illustrates a modification of the stereoscopic endoscope device in FIG. 1, and shows (a) a state where relatively long-range observation is performed, (b) an example of an image acquired at that time, (c) a state where a magnified image of the subject is observed without changing the distance thereto, and (d) an example of the magnified image acquired at that time.

The following description relates to a case where a magnified image of a small subject A, like an example image shown in FIG. 24(b), is to be observed when observing the subject A disposed at a distant position with a small internal angle α, as shown in FIG. 24(a). In this case, as shown in FIG. 24(c), the image capture elements 7 may be moved away from each other and inwardly pivoted by the translation mechanisms 24 while an intersecting point P of the optical axes 7a of the two image capture elements 7 is fixed on the subject A, thereby only increasing the internal angle α.

Accordingly, an image G3 of a magnified small region R including the subject A, like an example image shown in FIG. 24(d), can be acquired from an acquired image G. Since the acquired image G3 is equivalent to an image of a subject A' disposed at a close position acquired with an increased internal angle α, an appropriate stereoscopic effect can be obtained.

Although the above description relates to a case where the image capture elements 7 alone are pivoted or linearly moved, the image capture elements 7, the illumination elements 8, and the light-emitting element 9a and the light-receiving element 9b of the distance sensors 9 may be pivoted or linearly moved in an integral manner.

Furthermore, in addition to the two image capture elements 7 used for stereoscopic observation, another image capture element 38 having a wider field angle than the stereoscopic image capture elements 7 may be provided, as shown in FIG. 25(a), so that an image of the subject A that covers an area surrounding the stereoscopically-viewed area can also be acquired. Accordingly, with the wide-angle image, an operative field surrounding the stereoscopically-viewed subject A can also be checked, thereby facilitating the endoscopic operation.

In this case, the wide-angle image capture element 38 is preferably disposed near a plane including the optical axes of the two image capture elements 7. Accordingly, as shown in FIG. 25(b), a wide-angle field R1 can be brought closer to a stereoscopic field R2, thereby improving the ease of observation.

Furthermore, as shown in FIG. 26, each pivoting member 5 may be equipped with a plurality of image capture elements 7. In this case, a distance adjusting mechanism 29 that changes the distance between the image capture elements 7 may be provided. A linear actuator 30 may be used as the distance adjusting mechanism 29. In this case, the image processor 15 may have a function for generating a stereoscopic image on the basis of multiple images acquired at different distances.

As shown in FIGS. 26(a) and 26(b), by activating the distance adjusting mechanism 29, the image processor 15 can perform processing for generating polygonal data from multiple images of different visual points acquired at different distances so as to generate a new stereoscopic image. The generated new stereoscopic image can be enlarged, reduced, or rotated by image processing. This allows for improved ease of observation.

In this embodiment, the internal angle α is adjusted by moving the two image capture elements 7. Alternatively, from a pair of left and right parallax images G1 and G2 acquired by the two image capture elements 7, as shown in FIGS. 27(a) to 27(c), images G1' and G2' centered on an observation site F may be cut out, as shown in FIG. 28.

Figure 27:
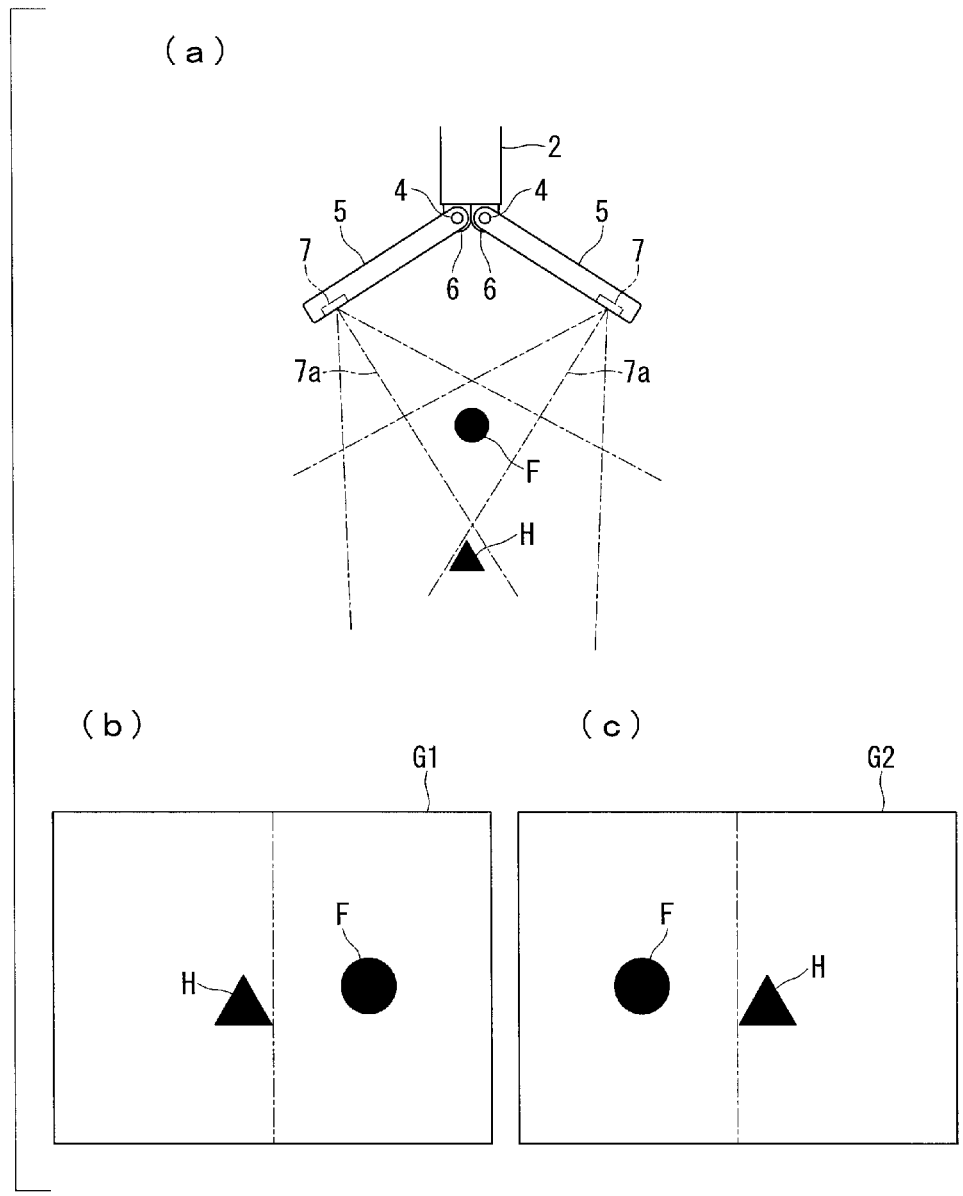
FIG. 27 illustrates a modification of the stereoscopic endoscope device in FIG. 1, and shows (a) the stereoscopic endoscope device, (b) an example of a left image, and (c) an example of a right image, which are used for acquiring an image having appropriate parallax by image processing without moving the image capture elements.
Figure 28:
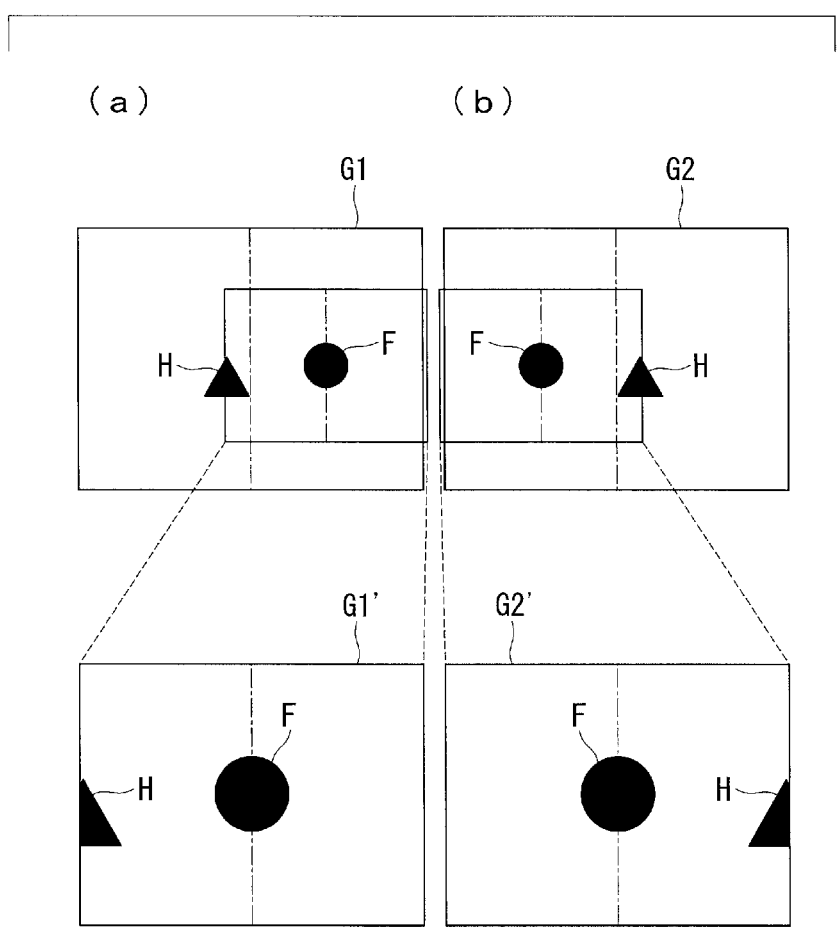
FIG. 28 illustrates (a) a left image and (b) a right image for explaining the image processing performed by the stereoscopic endoscope device in FIG. 27.

Reference character H in FIGS. 27 and 28 denotes a non-observation site.

Accordingly, as shown in FIGS. 28(a) and 28(b), appropriate parallax images G1' and G2' having the observation site F in the center can be acquired without having to move the image capture elements 7.

In this case, the subject A disposed in the center of each of the images G1' and G2' may be designated manually, or may be set automatically by image processing based on morphological characteristics or the like.

In this embodiment, the timing at which the pivoting members 5 are to be pivoted when inserted into the body is set by the distal-end distance sensors 10 disposed at the distal ends of the pivoting members 5. Alternatively, any type of sensor that detects that the pivoting members 5 are entirely inserted into the body may be provided in the insertion section 2, as shown in FIG. 29. In the example shown, a $CO_2$ sensor 31 is provided closer to the base end than the pivoting members 5 are.

Because the $CO_2$ concentration inside the body is 0.5% whereas the $CO_2$ concentration outside the body is 0.06%, it is readily detectable whether or not the pivoting members 5 are inserted into the body on the basis of a difference in $CO_2$ concentration detected by the $CO_2$ sensor 31.

According to the above embodiments, following aspects can be introduced.

An aspect of the present invention provides a stereoscopic endoscope device including two image capture elements spaced apart from each other and disposed in an insertion section to be inserted into a subject; an angle changing mechanism that changes a relative angle between optical axes of the image capture elements; a distance sensor that detects a distance from the image capture elements to the subject; and a controller that controls the angle changing mechanism on the basis of the distance detected by the distance sensor.

According to the aspect of the invention, when the insertion section is inserted into the subject and is brought close to the subject, the distance sensor provided in the insertion section detects the distance from the image capture elements to the subject, and the controller controls the angle changing mechanism on the basis of the detected distance. Because the angle changing mechanism changes the relative angle between the optical axes of the two image capture elements, an internal angle between the two image capture elements is adjusted in accordance with the distance from the image capture elements to the subject, whereby an appropriate stereoscopic image of the subject can be automatically acquired.

In the above aspect, the controller may control the angle changing mechanism so that an intersecting point of the optical axes of the image capture elements coincides with a surface of the subject.

Accordingly, the intersecting point of the optical axes of the image capture elements can be made to coincide with the surface of the subject (and can also be arbitrarily set) on the basis of the distance detected by the distance sensor, whereby an appropriate stereoscopic image of the subject can be automatically acquired.

Furthermore, in the above aspect, the controller may include a storage section that stores a map in which the distance and information indicating the relative angle are in correspondence with each other, and, on the basis of the map, controls the angle changing mechanism so that the relative angle indicated in the information corresponding to the distance detected by the distance sensor is achieved.

Accordingly, the relative angle indicated in the information stored in advance in the map is achieved on the basis of the distance detected by the distance sensor. Consequently, an appropriate internal angle can be quickly achieved, whereby an appropriate stereoscopic image of the subject can be quickly acquired.

Furthermore, in the above aspect, the distance and the information indicating the relative angle that are in correspondence with each other in the map may have a relationship such that the relative angle changes continuously relative to the distance.

Accordingly, the relative angle between the optical axes of the image capture elements is adjusted every time there is a change in the distance detected by the distance sensor, whereby an appropriate stereoscopic image of the subject can always be acquired.

Furthermore, in the above aspect, the distance and the information indicating the relative angle that are in correspondence with each other in the map may have a relationship such that the relative angle changes in a stepwise fashion relative to the distance.

Accordingly, the relative angle between the optical axes of the image capture elements is prevented from changing frequently due to a change in the distance detected by the distance sensor, thereby preventing fluctuations in the acquired image and improving the ease of observation.

Furthermore, in the above aspect, the distance and the information indicating the relative angle that are in correspondence with each other in the map may have a relationship such that the relative angle changes relative to different distances between when the distance changes in an increasing direction and when the distance changes in a decreasing direction.

Accordingly, when the distance between the insertion section and the subject increases or decreases, the relative angle between the optical axes of the image capture elements is prevented from changing frequently, thereby preventing fluctuations in the acquired image and improving the ease of observation.

Furthermore, in the above aspect, the controller may include a plurality of the maps with different correspondence relationships between the distance and the information, and the stereoscopic endoscope device may further include a map selecting section to be used by an observer for selecting any one of the maps.

Accordingly, the observer can select any one of the maps via the map selecting section so that the angle changing mechanism can perform an appropriate operation in accordance with the type of subject.

Furthermore, in the above aspect, the plurality of the maps may indicate different relative angles when the distance is at a minimum.

Accordingly, the internal angle between the two image capture elements corresponding to a position where the insertion section is disposed closest to the subject can be selected via the map selecting section, whereby the stereoscopic effect can be adjusted when observing a magnified image of the subject.

Furthermore, in the above aspect, the angle changing mechanism may include at least one pivoting member attached to a distal end of the insertion section in a pivotable manner around an axis extending in a direction intersecting a longitudinal axis of the insertion section, and a driving section that causes the pivoting member to pivot. In this case, one of the image capture elements may be attached to the pivoting member.

Accordingly, the pivoting member is pivoted by activating the driving section constituting the angle changing mechanism, whereby the relative angle between the optical axes of the two image capture elements can be readily changed.

Furthermore, in the above aspect, the angle changing mechanism may include a pair of the pivoting members, and the image capture elements may respectively be attached to the pivoting members.

Accordingly, the optical axes of the two image capture elements are shifted by causing the pair of the pivoting members to pivot, whereby the relative angle between the optical axes of the two image capture elements can be readily changed.

Furthermore, in the above aspect, the driving section may cause the pair of the pivoting members to pivot between a closed position in which the pivoting members have moved toward each other so as to extend along a longitudinal axis of the insertion section, and an open position in which the pivoting members have moved away from each other so as to extend in the direction intersecting the longitudinal axis of the insertion section.

Accordingly, when the insertion section is to be inserted into the subject, the pivoting members are disposed in the closed position so as to extend in the longitudinal direction of the insertion section, thereby reducing the cross-sectional area thereof and facilitating the inserting process. After the distal end of the insertion section is inserted into the subject, the pivoting members are pivoted so as to be disposed in the open position, thereby ensuring a sufficient distance between the image capture elements and readily forming a large internal angle.

Furthermore, in the above aspect, the driving section may cause the pivoting members to pivot independently of each other.

Accordingly, the optical axes of the two image capture elements can be not only set on the extension of the insertion section but also oriented in different directions, so that the subject is observable not only from the front but also from an angle or from the side.

Furthermore, in the above aspect, the angle changing mechanism may include an element pivoting mechanism that causes the image capture elements to pivot relative to the pivoting member within a pivot plane of the pivoting member.

Accordingly, based on the distance detected by the distance sensor, the pair of the pivoting members is pivoted by activating the driving section, and the image capture elements are pivoted by activating the element pivoting mechanism, whereby different relative angles with respect to various intersecting points between the optical axes of the two image capture elements can be achieved. Consequently, the subject can be observed with different stereoscopic effects.

Furthermore, in the above aspect, the stereoscopic endoscope device may further include a distance adjusting mechanism that changes the distance between the image capture elements.

Accordingly, the pivoting member is pivoted by activating the angle changing mechanism so that the relative angle between the optical axes of the two image capture elements is adjusted. In addition, the distance between the image capture elements is changed by activating the distance adjusting mechanism, whereby different relative angles with respect to various intersecting points between the optical axes of the two image capture elements can be achieved.

Consequently, when the subject to be observed is located at a distant position, the subject can be observed with an internal angle used for observing a subject located at a close position, so that an appropriate stereoscopic effect can be obtained when observing a magnified version of the acquired image. Although the pivoting member approaching a subject during observation of a subject located at a close position could conceivably become a hindrance to the observation of the subject since the relative angle of the pivoting member becomes small when a large internal angle is to be achieved, the above configuration can achieve a stereoscopic effect similar to that when observing a subject located at a close position, while the pivoting member is sufficiently distant from the subject. On the other hand, when observing a subject located at a close position, the subject can be observed with an internal angle used when observing a subject located at a distant position, whereby an appropriate stereoscopic effect can be obtained when observing a reduced version of the acquired image.

Furthermore, in the above aspect, the stereoscopic endoscope device may further include a stereoscopic-image generating section that generates a stereoscopic image on the basis of a plurality of images acquired at different distances by changing the distance between the image capture elements by using the distance adjusting mechanism.

Accordingly, a stereoscopic image can be generated from a plurality of images acquired by the plurality of image capture elements with different visual points.

Furthermore, in the above aspect, the stereoscopic endoscope device may further include a closed-position distance sensor that detects a distance from distal ends of the pivoting members to the subject when the pivoting members are disposed in the closed position.

Accordingly, when the insertion section is to be inserted into the subject, the pivoting members are disposed in the closed position so that the cross-sectional area thereof is reduced. Even in this case, the closed-position distance sensor can detect the distance from the distal ends of the pivoting members to the subject, so that the distal ends of the pivoting members, when inserted into the subject, are prevented from coming into contact with the subject.

Furthermore, in the above aspect, the insertion section may include a $CO_2$ sensor provided closer to a base end thereof than the pivoting members are.

Accordingly, when the $CO_2$ sensor detects a $CO_2$ concentration that is higher than or equal to a predetermined value, the $CO_2$ sensor can detect that the pivoting members, which are located closer to the distal end than the $CO_2$ sensor is, are completely inserted into the subject.

The present invention is advantageous in that an appropriate stereoscopic image of a subject can be readily acquired.

REFERENCE SIGNS LIST

A subject
α internal angle (relative angle)
1 stereoscopic endoscope device
2 insertion section
5 pivoting member (angle changing mechanism)
6 rotary micro-actuator (driving section, angle changing mechanism)
7 image capture element
7a optical axis
9 distance sensor
10 distal-end distance sensor (closed-position distance sensor)
14 pivot controller (controller)
15 image processor (stereoscopic-image generating section)
17 map storage section (storage section)
20 image-capture-element pivoting mechanism (element pivoting mechanism, angle changing mechanism)
24 translation mechanism (distance adjustment mechanism)
31 $CO_2$ sensor

The invention claimed is:
1. A stereoscopic endoscope device comprising:
two imaging sensors spaced apart from each other and disposed in an insertion section to be inserted into a subject;
an angle changing mechanism that changes a relative angle between optical axes of the imaging sensors;
a distance sensor that detects a distance from the imaging sensors to the subject; and
a controller that controls the angle changing mechanism on the basis of the distance detected by the distance sensor,
wherein the controller includes a memory that stores a map in which the distance and information indicating the relative angle are in correspondence with each other, and, on the basis of the map, controls the angle changing mechanism so that the relative angle indi- cated in the information corresponding to the distance detected by the distance sensor is achieved, the distance and the information indicating the relative angle that are in correspondence with each other in the map have a relationship such that the relative angle changes in a stepwise fashion relative to the distance, and the distance and the information indicating the relative angle that are in correspondence with each other in the map have a relationship such that the relative angle changes relative to different distances between when the distance changes in an increasing direction and when the distance changes in a decreasing direction.

2. The stereoscopic endoscope device according to claim 1, wherein the controller controls the angle changing mechanism so that an intersecting point of the optical axes of the imaging sensors coincides with a surface of the subject.

3. The stereoscopic endoscope device according to claim 1, wherein the controller includes a plurality of the maps with different correspondence relationships between the distance and the information, and wherein the stereoscopic endoscope device further comprises a map selecting section to be used by an observer for selecting any one of the maps.

4. The stereoscopic endoscope device according to claim 3, wherein the plurality of the maps indicate different relative angles when the distance is at a minimum.

5. The stereoscopic endoscope device according to claim 1, wherein the angle changing mechanism includes at least one pivoting member attached to a distal end of the insertion section in a pivotable manner around an axis extending in a direction intersecting a longitudinal axis of the insertion section, and a driving section that causes the pivoting member to pivot, and wherein one of the imaging sensors is attached to the pivoting member.

6. The stereoscopic endoscope device according to claim 5, wherein the angle changing mechanism includes a pair of the pivoting members, and wherein the imaging sensors are respectively attached to the pivoting members.

7. The stereoscopic endoscope device according to claim 6, wherein the driving section causes the pair of the pivoting members to pivot between a closed position in which the pivoting members have moved toward each other so as to extend along a longitudinal axis of the insertion section, and an open position in which the pivoting members have moved away from each other so as to extend in the direction intersecting the longitudinal axis of the insertion section.

8. The stereoscopic endoscope device according to claim 7, further comprising a closed-position distance sensor that detects a distance from distal ends of the pivoting members to the subject when the pivoting members are disposed in the closed position.

9. The stereoscopic endoscope device according to claim 7, wherein the insertion section includes a $CO_2$ sensor provided closer to a base end thereof than the pivoting members are.

10. The stereoscopic endoscope device according to claim 6, wherein the driving section causes the pivoting members to pivot independently of each other.

11. The stereoscopic endoscope device according to claim 5, wherein the angle changing mechanism includes an element pivoting mechanism that causes the imaging sensors to pivot relative to the pivoting member within a pivot plane of the pivoting member.

12. The stereoscopic endoscope device according to claim 11, further comprising a distance adjusting mechanism that changes the distance between the imaging sensors.

13. The stereoscopic endoscope device according to claim 12, wherein the controller further generates a stereoscopic image on the basis of a plurality of images acquired at different distances by changing the distance between the imaging sensors by using the distance adjusting mechanism.

* * * * *